(12) United States Patent
Kashu et al.

(10) Patent No.: US 10,177,358 B2
(45) Date of Patent: *Jan. 8, 2019

(54) FILM PRODUCTION METHOD AND FILM PRODUCTION DEVICE

(71) Applicant: Sumitomo Chemical Company, Limited, Tokyo (JP)

(72) Inventors: Koji Kashu, Niihama (JP); Yusuke Kon, Daegu (KR); Tatsuya Sakamoto, Niihama (JP); Jian Wang, Daegu (KR)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/517,818

(22) PCT Filed: Sep. 18, 2015

(86) PCT No.: PCT/JP2015/076652
§ 371 (c)(1),
(2) Date: Apr. 7, 2017

(87) PCT Pub. No.: WO2016/056380
PCT Pub. Date: Apr. 14, 2016

(65) Prior Publication Data
US 2017/0307971 A1  Oct. 26, 2017

(30) Foreign Application Priority Data

Oct. 10, 2014 (JP) .................................. 2014-209414
Jan. 30, 2015 (WO) .................. PCT/JP2015/052749

(51) Int. Cl.
*G01N 21/894* (2006.01)
*H01M 2/14* (2006.01)
(Continued)

(52) U.S. Cl.
CPC ............ *H01M 2/145* (2013.01); *B26D 1/035* (2013.01); *B26D 7/14* (2013.01); *B26D 7/2614* (2013.01);
(Continued)

(58) Field of Classification Search
None
See application file for complete search history.

(56) References Cited

U.S. PATENT DOCUMENTS 3,806,015 A    4/1974   Kachioff et al.
5,523,848 A    6/1996   Musso et al.
(Continued)

FOREIGN PATENT DOCUMENTS

CN    1804601 A    7/2006
CN    1873398 A    12/2006
(Continued)

OTHER PUBLICATIONS

Office Action dated Sep. 25, 2017 in CN Application No. 201580054773.
(Continued)

*Primary Examiner* — Andre Allen
(74) *Attorney, Agent, or Firm* — Panitch Schwarze Belisario & Nadel LLP

(57) ABSTRACT

A method for film production includes the steps of obtaining information on the position of a defect (D) in a separator (12a) and providing marks (LA, LB) at the respective positions in the vicinity of the defect (D), the marks indicating the position of the defect.

9 Claims, 17 Drawing Sheets

(51) Int. Cl.

| | | |
|---|---|---|
| *B26D 7/14* | (2006.01) | |
| *B26D 7/26* | (2006.01) | |
| *B65H 16/10* | (2006.01) | |
| *B65H 18/08* | (2006.01) | |
| *B65H 26/02* | (2006.01) | |
| *G01N 21/892* | (2006.01) | |
| *G03B 1/04* | (2006.01) | |
| *G03B 1/42* | (2006.01) | |
| *G03B 1/56* | (2006.01) | |
| *G03B 17/30* | (2006.01) | |
| *G03B 17/42* | (2006.01) | |
| *G03B 21/32* | (2006.01) | |
| *H01M 10/0525* | (2010.01) | |
| *B26D 1/03* | (2006.01) | |
| *H01M 2/16* | (2006.01) | |
| *G03B 17/00* | (2006.01) | |
| *G03B 21/00* | (2006.01) | |

(52) U.S. Cl.
CPC ............. *B65H 16/10* (2013.01); *B65H 18/08* (2013.01); *B65H 26/02* (2013.01); *G01N 21/892* (2013.01); *G01N 21/894* (2013.01); *G03B 1/04* (2013.01); *G03B 1/42* (2013.01); *G03B 1/56* (2013.01); *G03B 17/30* (2013.01); *G03B 17/425* (2013.01); *G03B 21/328* (2013.01); *H01M 2/1653* (2013.01); *H01M 2/1686* (2013.01); *H01M 10/0525* (2013.01); *B65H 2557/62* (2013.01); *G03B 17/00* (2013.01); *G03B 21/00* (2013.01); *G03B 2217/243* (2013.01); *H01M 2/166* (2013.01)

(56) References Cited

U.S. PATENT DOCUMENTS

| | | | | |
|---|---|---|---|---|
| 6,219,930 | B1 * | 4/2001 | Reid | ................ G01B 3/14 |
| | | | | 33/1 BB |
| 2004/0251176 | A1 | 12/2004 | Alonso et al. | |
| 2006/0164647 | A1 | 7/2006 | Shibata | |
| 2008/0087149 | A1 | 4/2008 | Ohashi | |
| 2010/0294418 | A1 | 11/2010 | Yura et al. | |
| 2011/0085125 | A1 | 4/2011 | Kimura et al. | |
| 2012/0002153 | A1 | 1/2012 | Kimura et al. | |
| 2012/0002154 | A1 | 1/2012 | Kimura et al. | |
| 2012/0028067 | A1 | 2/2012 | Izaki et al. | |
| 2012/0055607 | A1 | 3/2012 | Kitagawa et al. | |
| 2012/0055608 | A1 | 3/2012 | Kitagawa et al. | |
| 2012/0055621 | A1 | 3/2012 | Goto et al. | |
| 2012/0055622 | A1 | 3/2012 | Kitagawa et al. | |
| 2012/0055623 | A1 | 3/2012 | Kitagawa et al. | |
| 2012/0056211 | A1 | 3/2012 | Kitagawa et al. | |
| 2012/0056340 | A1 | 3/2012 | Kitagawa et al. | |
| 2012/0057104 | A1 | 3/2012 | Kitagawa et al. | |
| 2012/0057107 | A1 | 3/2012 | Kitagawa et al. | |
| 2012/0057231 | A1 | 3/2012 | Goto et al. | |
| 2012/0057232 | A1 | 3/2012 | Goto et al. | |
| 2012/0058291 | A1 | 3/2012 | Kitagawa et al. | |
| 2012/0058321 | A1 | 3/2012 | Goto et al. | |
| 2013/0100529 | A1 | 4/2013 | Kitagawa et al. | |
| 2013/0114139 | A1 | 5/2013 | Kitagawa et al. | |
| 2013/0169956 | A1 | 7/2013 | Cano Cediel et al. | |
| 2014/0014762 | A1 | 1/2014 | Ichinomiya et al. | |
| 2014/0186568 | A1 | 7/2014 | Kitagawa et al. | |
| 2014/0287255 | A1 | 9/2014 | Izaki et al. | |
| 2015/0183199 | A1 | 7/2015 | Kitagawa et al. | |
| 2016/0054494 | A1 | 2/2016 | Kitagawa et al. | |
| 2016/0103258 | A1 | 4/2016 | Kitagawa et al. | |
| 2016/0377416 | A1 * | 12/2016 | Reid | ............ G01B 11/2513 |
| | | | | 356/612 |
| 2017/0317327 | A1 * | 11/2017 | Kashu | ................ H01M 2/145 |

FOREIGN PATENT DOCUMENTS

| | | |
|---|---|---|
| CN | 101468543 A | 7/2009 |
| CN | 101925944 A | 12/2010 |
| CN | 101980797 A | 2/2011 |
| CN | 101981438 A | 2/2011 |
| CN | 102043280 A | 5/2011 |
| CN | 102341733 A | 2/2012 |
| CN | 102385086 A | 3/2012 |
| CN | 102385087 A | 3/2012 |
| CN | 102866168 A | 1/2013 |
| JP | H8101130 | 4/1996 |
| JP | 2002228429 A | 8/2002 |
| JP | 2004338406 A | 12/2004 |
| JP | 2004338409 A | 12/2004 |
| JP | 2006194721 A | 7/2006 |
| JP | 2006220527 A | 8/2006 |
| JP | 200882910 A | 4/2008 |
| JP | 2008116437 A | 5/2008 |
| JP | 2009133741 A | 6/2009 |
| JP | 2009244063 A | 10/2009 |
| JP | 201032346 A | 2/2010 |
| JP | 2011220967 A | 11/2011 |
| JP | 201333033 A | 2/2013 |

OTHER PUBLICATIONS

Office Action dated Oct. 10, 2017 in CN Application No. 201580054771.1.
Int'l Preliminary Report on Patentability dated Apr. 20, 2017 in Int'l Application No. PCT/JP2015/076652.
Int'l Preliminary Report on Patentability dated Apr. 20, 2017 in Int'l Application No. PCT/JP2015/076651.
Int'l Preliminary Report on Patentability dated Apr. 20, 2017 in Int'l Application No. PCT/JP2015/076650.
Int'l Preliminary Report on Patentability dated Apr. 20, 2017 in Int'l Application No. PCT/JP2015/052749.
Office Action dated Apr. 7, 2015 in JP Application No. 2015-506030 (Partial Translation).
Office Action dated Dec. 11, 2017 in U.S. Appl. No. 15/517,199, by Kashu.
Office Action dated Nov. 28, 2017 in CN Application No. 201580056172.3.
Int'l Search Report dated Dec. 8, 2015 in In'l Application No. PCT/JP2015/076652.
Int'l Search Report dated Dec. 8, 2015 in Int'l Application No. PCT/JP2015/076651.
Int'l Search Report dated Dec. 8, 2015 in Int'l Application No. PCT/JP2015/076650.
Int'l Search Report dated Apr. 14, 2015 in In'l Application No. PCT/JP2015/052749.
Office Action dated Jun. 14, 2016 in JP Application No. 2016-520128.
Decision to Grant dated Sep. 6, 2016 in JP Application No. 2016-520128.
Office Action dated Jun. 14, 2016 in JP Application No. 2016-520129.
Decision to Grant dated Sep. 6, 2016 in JP Application No. 2016-520129.
Office Action dated Jun. 14, 2016 in JP Application No. 2016-520115.
Decision to Grant dated Sep. 6, 2016 in JP Application No. 2016-520115.
Office Action dated Feb. 11, 2018 in CN Application No. 201580054773.0.
Office Action dated Sep. 19, 2018 in U.S. Appl. No. 15/517,249 by Watanabe.

* cited by examiner

FILM PRODUCTION METHOD AND FILM PRODUCTION DEVICE

CROSS-REFERENCE TO RELATED APPLICATION

This application is a Section 371 of International Application No. PCT/JP2015/076652, filed Sep. 18, 2015, which was published in the Japanese language on Apr. 14, 2016 under International Publication No. WO 2016/056380 A1, and the disclosure of which is incorporated herein by reference.

TECHNICAL FIELD

The present invention relates to a film producing method, a film producing apparatus, a film, and a film roll.

BACKGROUND ART

There has been known a deficiency inspecting device for a sheet-shaped product including an optical film (Patent Literature 1). The deficiency inspecting device receives information on a deficiency from a protective film inspecting section, and forms a data code (for example, a two-dimensional code or a QR Code [registered trademark]) having a fixed pitch and indicative of the deficiency. The deficiency inspecting device forms such a data code on a surface at an end of a PVA film original sheet together with information on the position and production identification.

Further, there has been known a defect indicating method for specifying a defective portion of a sheet of paper, the method including cutting a sheet of paper to divide it into a plurality of narrower sheets of paper and providing a visible indicator at a portion corresponding to a defect in a sheet of paper as divided (see Patent Literature 2).

CITATION LIST

Patent Literature

[Patent Literature 1] Japanese Patent Application Publication, Tokukai, No. 2008-116437 (Publication date: May 22, 2008)
[Patent Literature 2] Japanese Patent Application Publication, Tokukai, No. 2008-82910 (Publication date: Apr. 10, 2008)

SUMMARY OF INVENTION

Technical Problem

For a film producing process, however, merely providing a marking to a portion corresponding to a defect as in Patent Literature 2 does not make it possible to accurately determine the area of the defect in the film. Thus, cutting off a portion of a film on the basis of a marking to, for example, remove a defect may, depending on the size of a defect in the film, fail to cut off the entire area of the defect, leaving a defective portion in the film.

It is an object of an embodiment of the present invention to provide a film producing method, a film producing apparatus, a film, and a film roll each of which makes it possible to accurately indicate the area of a defect in a film.

Solution to Problem

In order to attain the above object, a film producing method in accordance with an embodiment of the present invention includes the steps of: (a) obtaining information on a position of at least one defect in a film; and (b) providing a plurality of markings at respective positions in a vicinity of the at least one defect, the plurality of markings indicating the position of the at least one defect.

The above production method includes providing a plurality of markings in the vicinity of a defect. This makes it possible to show the area of the defect in the film more accurately than in a case where only one marking is provided in the vicinity of a defect. With the above arrangement, cutting off a portion of the film on the basis of the markings, for example, can remove the defect from the film appropriately.

The film producing method in accordance with an embodiment of the present invention may be arranged such that in the step (b), the plurality of markings include a pair of markings provided in such a manner that one of the pair of markings lies on a first side of the at least one defect in a longitudinal direction of the film and that the other of the pair of markings lies on a second side of the at least one defect in the longitudinal direction of the film.

The above production method makes it possible to more accurately show the area of a defect in the longitudinal direction of the film. With this arrangement, cutting off a portion of the film which portion has a length indicated by the markings in the longitudinal direction can remove the defect from the film appropriately.

The film producing method in accordance with an embodiment of the present invention may be arranged such that in a case where the at least one defect includes a plurality of defects apart from each other in the longitudinal direction of the film by a distance of less than a predetermined value, a first marking out of the pair of markings is provided on the first side of a first defect out of the plurality of defects which first defect is farthest on the first side, and a second marking out of the pair of markings is provided on the second side of a second defect out of the plurality of defects which second defect is farthest on the second side.

The above production method makes it possible to, in a case where there are a plurality of defects, show the area of those defects with use of a pair of markings. This can reduce the number of markings to be provided. The above production method also makes it possible to, in a case where a portion of a film is cut off for removal of a defect, reduce the respective numbers of cutting positions and cutting operations necessary to produce a film having no defect and a length of not less than a predetermined value.

The film producing method in accordance with an embodiment of the present invention may be arranged such that in the step (a), the information on the position indicates presence or absence of defectiveness in each of a plurality of unit regions each having a predetermined length in the longitudinal direction of the film, and in the step (b), the pair of markings are provided in such a manner that one of the pair of markings lies on the first side, in the longitudinal direction of the film, of a unit region out of the plurality of unit regions which unit region has the at least one defect and that the other of the pair of markings lies on the second side, in the longitudinal direction of the film, of the unit region having the defect.

The above production method makes it possible to show the area of a defect in each unit region in correspondence with simple information on the position of the defect in that unit region.

The film producing method in accordance with an embodiment of the present invention may further include the steps of: (c) obtaining original sheet defect position information indicative of a position of a defect in a film original sheet; and (d) slitting the film original sheet along a slit line, extending in a longitudinal direction of the film original sheet, so as to produce a plurality of films.

The above production method makes it possible to produce a plurality of films from a single film original sheet for improved film production.

The film producing method in accordance with an embodiment of the present invention may be arranged such that in the step (a), the information on the position is obtained on a basis of the original sheet defect position information; and in the step (b), the plurality of markings are provided to the film on a basis of the information on the position.

The above production method eliminates the need to detect defects in each of the plurality of films to obtain positional information, but simply needs to detect defects in a film original sheet to obtain information on the respective positions of the defects in the film original sheet. This can simplify the film producing process.

The film producing method in accordance with an embodiment of the present invention may be arranged such that in the step (b), the plurality of markings are provided to the film original sheet on a basis of the original sheet defect position information; and in the step (d), the film original sheet, to which the plurality of markings have been provided, is slit.

The above production method, which includes providing markings to a film original sheet before the slitting step, makes it possible to provide markings at correct positions in comparison to a case of providing markings to an individual film after the slitting step.

The film producing method in accordance with an embodiment of the present invention may be arranged such that in the step (b), the plurality of markings are so provided as not to overlap the slit line.

The above production method makes it possible to prevent a situation in which markings have been cut during the slitting step and it is consequently difficult to determine the area of a defect.

The film producing method in accordance with an embodiment of the present invention may be arranged such that in the step (b), at least one of the plurality of markings is provided in a vicinity of the at least one defect in a first one of two films adjacent to each other via the slit line, and at least one other of the plurality of markings is provided at a portion of a second one of the two films which portion corresponds to a position of the at least one of the plurality of markings.

With the above production method, even in a case where a film original sheet has been slit at positions different from desired slit positions, so that a defect is not present in a first film out of the two adjacent films in which first film the defect would otherwise be present and that the defect is present in a second film out of the two adjacent films, it is possible to reduce the risk of no markings being provided to indicate the position of the defect in the second film.

The film producing method in accordance with an embodiment of the present invention may be arranged such that in the step (c), the original sheet defect position information indicates presence or absence of defectiveness in each of a plurality of divisional regions arranged on a surface of the film original sheet in a width direction of the film original sheet, and in a case where in the step (d), the slit line divides at least one of the plurality of divisional regions which at least one divisional region has the at least one defect, in the step (b), the plurality of markings are provided to each of two films each including a divisional part of the at least one divisional region which divisional part results from slitting the film original sheet along the slit line.

In a case where a film original sheet is slit along a slit line dividing a divisional region, two films each including a divisional part of a divisional region having a defect are both likely to have the defect. The above production method includes providing markings to two films likely to have a defect. This makes it possible to reduce the risk of no markings being provided to indicate the position of a defect in a film.

In order to attain the above object, a film producing apparatus in accordance with an embodiment of the present invention includes: a defect information obtaining section configured to obtain information on a position of a defect in a film; and a defect marking providing section configured to provide a plurality of markings at respective positions in a vicinity of the defect, the plurality of markings indicating the position of the defect.

In order to attain the above object, a film in accordance with an embodiment of the present invention includes a plurality of markings at respective positions in a vicinity of a defect, the plurality of markings indicating a position of the defect.

With the above arrangement, a plurality of markings are provided in the vicinity of a defect. This makes it possible to show the area of the defect more accurately than in a case where only one marking is provided in the vicinity of a defect.

The film in accordance with an embodiment of the present invention may be arranged such that the plurality of markings include a pair of markings provided in such a manner that one of the pair of markings lies on a first side of the defect in a longitudinal direction of the film and that the other of the pair of markings lies on a second side of the defect in the longitudinal direction of the film.

The above arrangement makes it possible to more accurately show the area of a defect in the longitudinal direction of the film.

In order to attain the above object, a film in accordance with an embodiment of the present invention is one of a plurality of films corresponding respectively to a plurality of regions on a surface of a film original sheet having a defect which plurality of regions are defined by a boundary line extending in a longitudinal direction of the film original sheet, the film corresponding to a region out of the plurality of regions which region is adjacent, via the boundary line, to a region out of the plurality of regions which region has the defect, the film being provided with a plurality of markings in a vicinity of a position opposite to the defect across the boundary line.

With the above arrangement, in a case where a film original sheet is slit along a boundary line for production of a plurality of films corresponding respectively to the plurality of regions, it is possible to reduce the risk that a film that has ended up having a defect as a result of displacement of the slit positions from desired positions (the defect would otherwise be present in another film) is provided with no markings indicative of the position of the defect.

In order to attain the above object, a film roll in accordance with an embodiment of the present invention includes the film having been rolled up in a roll shape.

Rolling up a film into a film roll while the film is provided with markings at a position corresponding to a defect as described above makes it possible to easily handle the film and also to determine the position of the defect when the film is wound off.

Advantageous Effects of Invention

An embodiment of the present invention makes it possible to provide a film producing method, a film producing apparatus, a film, and a film roll each of which can reduce the possibility of making a defective film publicly available.

DESCRIPTION OF EMBODIMENTS

The following description will discuss embodiments of the present invention in detail.

Embodiment 1

The description below deals with, as an example film in accordance with an embodiment of the present invention, a separator and a heat-resistant separator for a battery such as a lithium-ion secondary battery. The description below further deals in order with a separator producing method and a separator producing apparatus as an example of a film producing method and a film producing apparatus in accordance with an embodiment of the present invention.

<Lithium-Ion Secondary Battery>

A nonaqueous electrolyte secondary battery, typically a lithium-ion secondary battery, has a high energy density, and is therefore currently widely used not only as batteries for use in devices such as personal computers, mobile phones, and mobile information terminals, and for use in moving bodies such as automobiles and airplanes, but also as stationary batteries contributing to stable power supply.

Figure 1:
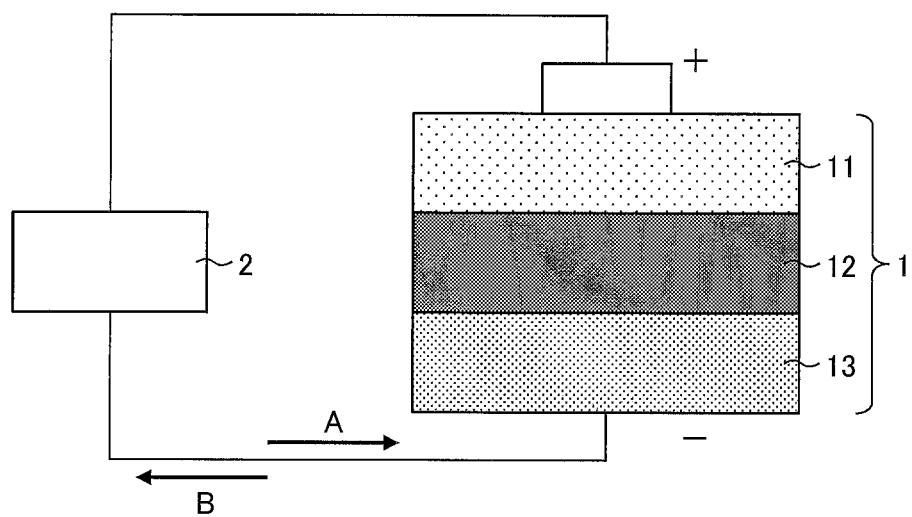
FIG. 1 is a diagram schematically illustrating a cross-sectional configuration of a lithium-ion secondary battery in accordance with Embodiment 1.

FIG. 1 is a diagram schematically illustrating a cross-sectional configuration of a lithium-ion secondary battery 1. As illustrated in FIG. 1, the lithium-ion secondary battery 1 includes a cathode 11, a separator 12, and an anode 13. Between the cathode 11 and the anode 13, an external device 2 is connected outside the lithium-ion secondary battery 1. While the lithium-ion secondary battery 1 is being charged, electrons move in a direction A. Meanwhile, while the lithium-ion secondary battery 1 is being discharged, electrons move in a direction B.

<Separator>

The separator 12 is provided so as to be sandwiched between the cathode 11 (as a positive electrode) and the anode 13 (as a negative electrode) of the lithium-ion secondary battery 1. While separating the cathode 11 and the anode 13, the separator 12, which is a porous film, allows lithium ions to move between the cathode 11 and the anode 13. The separator 12 contains, for example, a polyolefin (for example, polyethylene or polypropylene) as a material thereof.

Figure 2:
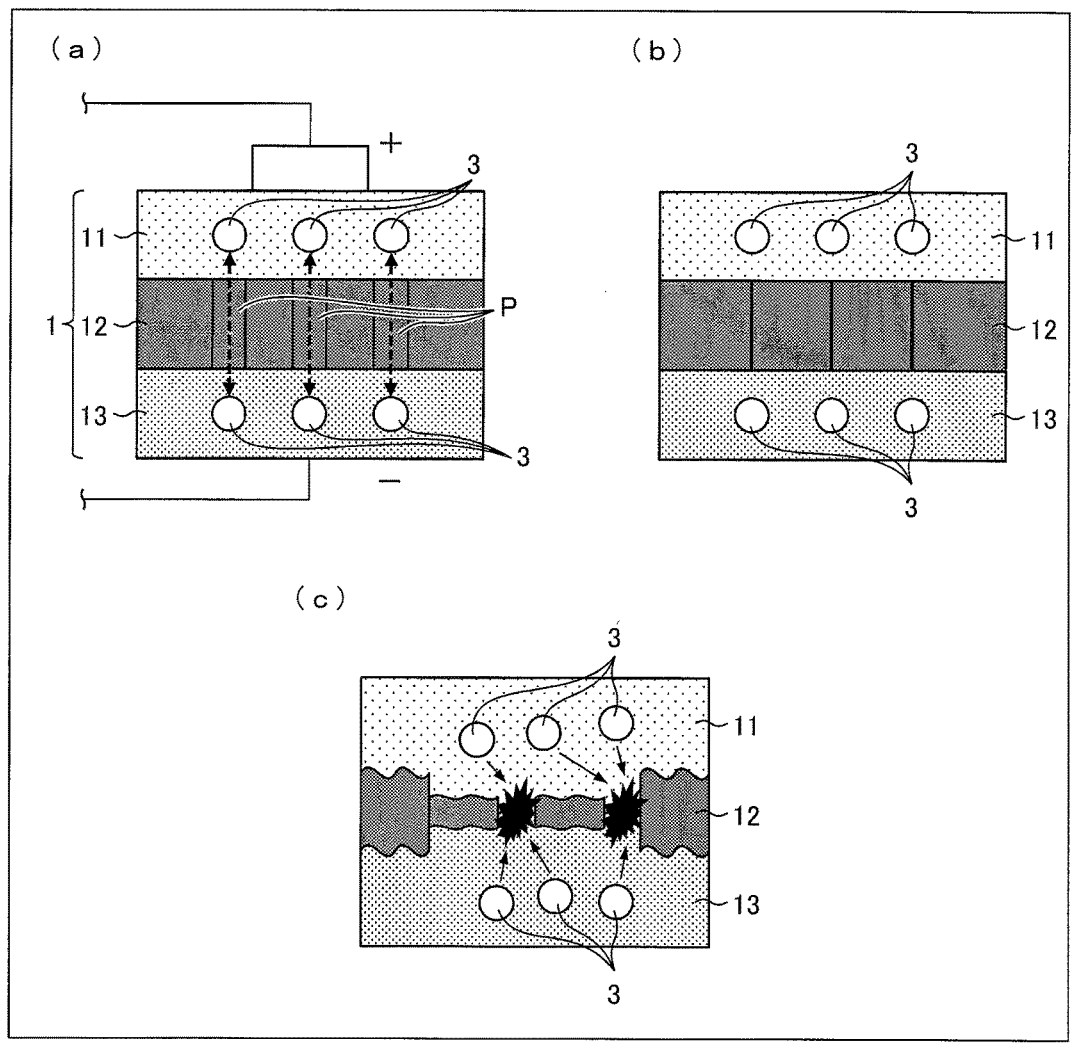
FIG. 2 provides diagrams schematically illustrating details of the configuration of the lithium-ion secondary battery illustrated in FIG. 1.

FIG. 2 provides diagrams schematically illustrating details of the configuration of the lithium-ion secondary battery 1 illustrated in FIG. 1. (a) of FIG. 2 illustrates a normal configuration. (b) of FIG. 2 illustrates a state in which the temperature of the lithium-ion secondary battery 1 has risen. (c) of FIG. 2 illustrates a state in which the temperature of the lithium-ion secondary battery 1 has sharply risen.

As illustrated in (a) of FIG. 2, the separator 12 is provided with many pores P. Normally, lithium ions 3 in the lithium-ion secondary battery 1 can move back and forth through the pores P.

Note here that there may be, for example, a case where the lithium-ion secondary battery 1 increases in temperature due to, for example, (i) overcharge of the lithium-ion secondary battery 1 or (ii) a large current caused by a short circuit having occurred in an external device. In such cases, the separator 12 melts or softens and the pores P are blocked as illustrated in (b) of FIG. 2. As a result, the separator 12 shrinks. This stops the movement of the lithium ions 3, and consequently stops the increase in temperature (described earlier).

Note, however, that the separator 12 suddenly shrinks in a case where the lithium-ion secondary battery 1 sharply increases in temperature. In this case, as illustrated in (c) of FIG. 2, the separator 12 may be broken. Then, the lithium ions 3 leak out from the separator 12 which has been broken, so that the lithium ions 3 do not stop moving back and forth. Thus, the increase in temperature continues.

<Heat-Resistant Separator>

Figure 3:
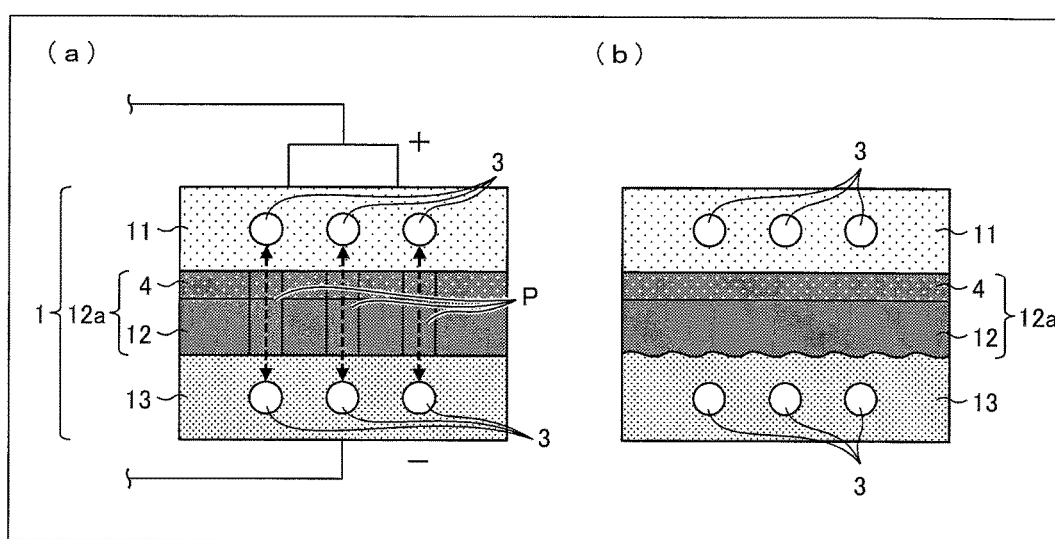
FIG. 3 provides diagrams schematically illustrating another configuration of the lithium-ion secondary battery illustrated in FIG. 1.

FIG. 3 provides diagrams schematically illustrating another configuration of the lithium-ion secondary battery 1 illustrated in FIG. 1. (a) of FIG. 3 illustrates a normal configuration, and (b) of FIG. 3 illustrates a state in which the temperature of the lithium-ion secondary battery 1 has sharply risen.

As illustrated in (a) of FIG. 3, the lithium-ion secondary battery 1 can further include a heat-resistant layer 4. The heat-resistant layer 4 and the separator 12 form a heat-resistant separator 12a (separator). The heat-resistant layer 4 is laminated on one surface of the separator 12 which surface is on the cathode 11 side. The heat-resistant layer 4 may alternatively be laminated on (i) a surface of the separator 12 which surface is on the anode 13 side or on (ii) both surfaces of the separator 12. Further, the heat-resistant layer 4 is provided with pores that are similar to the pores P. Normally, lithium ions 3 move back and forth through the pores P and the pores of the heat-resistant layer 4. The heat-resistant layer 4 contains, for example, wholly aromatic polyamide (aramid resin) as a material thereof.

As illustrated in (b) of FIG. 3, even in a case where the temperature of the lithium-ion secondary battery 1 has sharply risen and accordingly the separator 12 has melted or softened, the shape of the separator 12 is maintained because the heat-resistant layer 4 supports the separator 12. Thus, such a sharp increase in temperature merely results in melting or softening of the separator 12 and consequent blocking of the pores P. This stops the movement of the lithium ions 3, and consequently stops overdischarge and overcharge (described earlier). The separator 12 is thus prevented from being broken.

<Steps of Producing Heat-Resistant Separator Original Sheet (Separator Original Sheet)>

How to produce the heat-resistant separator 12a of the lithium-ion secondary battery 1 is not particularly limited. The heat-resistant separator 12a can be produced by a publicly known method. The following discussion assumes a case where the separator 12 contains polyethylene as a main material. However, even in a case where the separator 12 contains another material, the similar steps can still be applied to production of the heat-resistant separator 12a.

For example, it is possible to employ a method including the steps of first forming a film by adding an inorganic filler or plasticizer to a thermoplastic resin, and then removing the inorganic filler or plasticizer with an appropriate solvent. For example, in a case where the separator 12 is a polyolefin separator made of a polyethylene resin containing an ultrahigh molecular weight polyethylene, it is possible to produce a separator 12 by the following method.

This method includes (1) a kneading step of obtaining a polyethylene resin composition by kneading an ultrahigh molecular weight polyethylene with an inorganic filler (for example, calcium carbonate or silica) or plasticizer (for example, a low-molecular weight polyolefin or liquid paraffin), (2) a rolling step of forming a film from the polyethylene resin composition, (3) a removal step of removing the inorganic filler or plasticizer from the film obtained in the step (2), and (4) a stretching step of obtaining a separator 12 by stretching the film obtained in the step (3). The step (4) can alternatively be carried out between the steps (2) and (3).

In the removal step, many fine pores are provided in the film. The fine pores of the film stretched in the stretching step become the above-described pores P. The separator 12 formed as a result is a polyethylene microporous film having a prescribed thickness and a prescribed air permeability.

Note that the kneading step may involve kneading (i) 100 parts by weight of the ultrahigh molecular weight polyethylene, (ii) 5 parts by weight to 200 parts by weight of a low-molecular weight polyolefin having a weight-average molecular weight of 10000 or less, and (iii) 100 parts by weight to 400 parts by weight of the inorganic filler.

Thereafter, in a coating step, the heat-resistant layer 4 is formed on a surface of the separator 12. For example, on the separator 12, an aramid/NMP (N-methylpyrrolidone) solution (coating solution) is applied, and thereby, the heat-resistant layer 4 that is an aramid heat-resistant layer is formed. The heat-resistant layer 4 can be provided on only one surface or both surfaces of the separator 12. Alternatively, the heat-resistant layer 4 can be formed by using, for coating, a mixed solution containing a filler such as alumina/carboxymethyl cellulose.

Further, in the coating step, a polyvinylidene fluoride/dimethylacetamide solution (coating solution) can be applied (applying step) to a surface of the separator 12 and solidified (solidifying step) so that an adhesive layer is formed on the surface of the separator 12. The adhesive layer can be provided on only one surface or both surfaces of the separator 12.

A method for coating the separator 12 with a coating solution is not particularly limited as long as uniform wet coating can be performed by the method. The method can be a conventionally well-known method such as a capillary coating method, a spin coating method, a slit die coating method, a spray coating method, a dip coating method, a roll coating method, a screen printing method, a flexo printing method, a bar coater method, a gravure coater method, or a die coater method. The heat-resistant layer 4 has a thickness which can be controlled by adjusting (i) the thickness of a coating wet film, (ii) the solid-content concentration (which is the sum of concentrations of a binder and a filler in the coating solution), and/or (iii) the ratio of the filler to the binder.

It is possible to use a resin film, a metal belt, a drum or the like as a support with which the separator 12 is fixed or transferred in coating.

Figure 4:
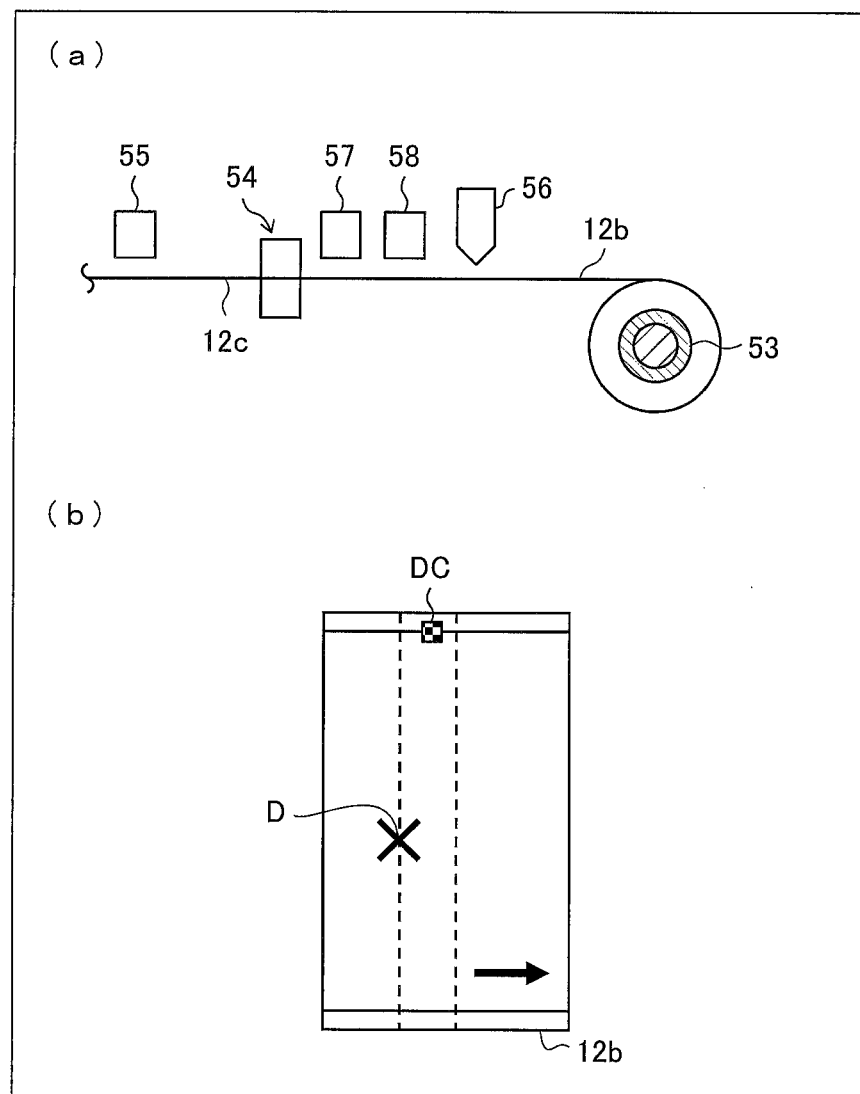
FIG. 4 provides diagrams schematically illustrating a defect detecting step and a defect information recording step both included in a method for marking a defect in a separator original sheet.

This operation allows for production of a heat-resistant separator original sheet 12b which is a separator original sheet 12c on which the heat-resistant layer 4 is laminated (see FIG. 4). The heat-resistant separator original sheet 12b thus produced is wound around a core 53 having a cylindrical shape (see FIG. 4). Note that the subject to be produced by the above production method is not limited to the heat-resistant separator original sheet 12b. The above production method does not necessarily include the coating step. In this case, the subject to be produced is a separator original sheet 12c. The description below mainly deals with an example of a heat-resistant separator (film) including a heat-resistant layer as a functional layer. A similar process (steps) can be carried out also for a separator (film) and separator original sheet (film original sheet) each including no functional layer.

<Defect Detecting Step>

In a case where during production of a heat-resistant separator for use in a lithium-ion secondary battery, an inspecting device has detected a defect in a coating step of preparing a heat-resistant separator original sheet including a separator original sheet coated with a heat-resistant layer, the original sheet having the defect is provided with a line drawn with a marker before the heat-resistant separator original sheet is wound up. In the subsequent slitting step, the heat-resistant separator original sheet is wound off. Then, when an operator sees the line drawn with the marker on the heat-resistant separator original sheet wound off, the operator stops the operation of winding off the heat-resistant separator original sheet. Next, the operator visually checks the position, along the width of the heat-resistant separator original sheet, of the defect indicated by the line drawn with the marker. Next, that portion of the heat-resistant separator original sheet on which the line is drawn with the marker is slit by a cutting device lengthwise to form a plurality of heat-resistant separators. Then, the operator attaches, to one of the heat-resistant separators, a piece of tape in such a manner that (i) the tape coincides with the lengthwise position on the heat-resistant separator at which position the defect indicated by the line drawn with the marker is present and that (ii) the tape extends beyond a side of the heat-resistant separator. The heat-resistant separator, to which the tape is attached in such a manner that the tape extends beyond a side of the heat-resistant separator, is wound up around a wind-up roller.

Next, the heat-resistant separator wound up around the wind-up roller is wound off from the wind-up roller and then wound up around an additional wind-up roller in an additional wind-up step. When an operator sees the tape in the additional wind-up step, the operator stops the operation of the additional wind-up step. The operator then cuts off, in the width direction, that portion of the heat-resistant separator at which the defect indicated by the tape is present, and removes that portion from the rest. Next, the heat-resistant separator on the side of the wind-up roller is connected with the heat-resistant separator on the side of the additional wind-up roller. Then, the operation of the additional wind-up step is resumed, so that the heat-resistant separator is all wound off from the wind-up roller and then wound up around the additional wind-up roller.

This procedure is, however, problematic in that it merely involves drawing a line on a heat-resistant separator original sheet with a marker in a case where an inspecting device has detected a defect in the heat-resistant separator original sheet. Thus, when an operator sees the line in the subsequent slitting step, the operator needs to stop the operation of winding off the heat-resistant separator original sheet and visually check the widthwise position of the defect. Enormous efforts are thus needed in order to specify the position of the defect in a plurality of heat-resistant separators prepared by slitting the heat-resistant separator original sheet.

Figure 5:
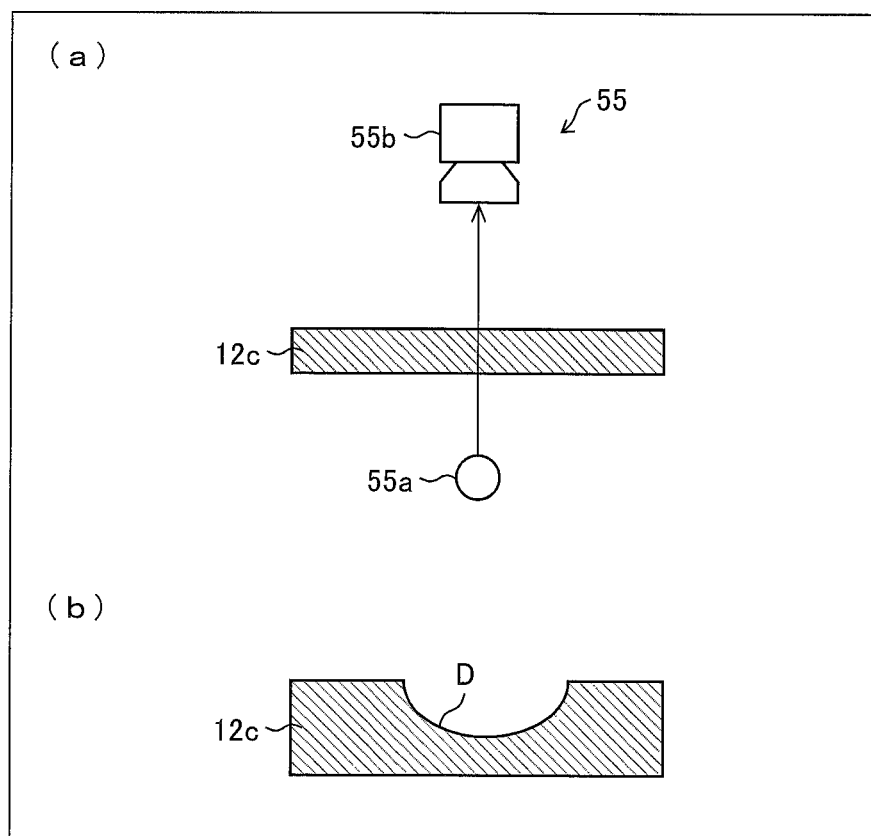
FIG. 5 provides diagrams illustrating a configuration of a base material defect inspecting device in the defect detecting step.
Figure 6:
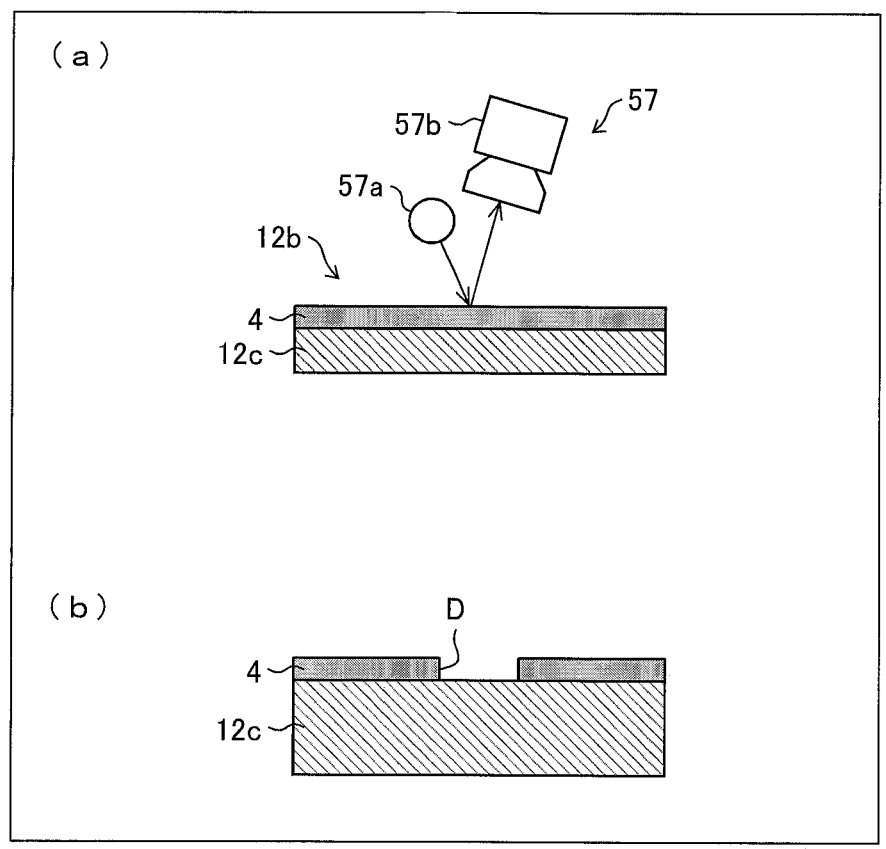
FIG. 6 provides diagrams illustrating a configuration of a coating defect inspecting device in the defect detecting step.
Figure 7:
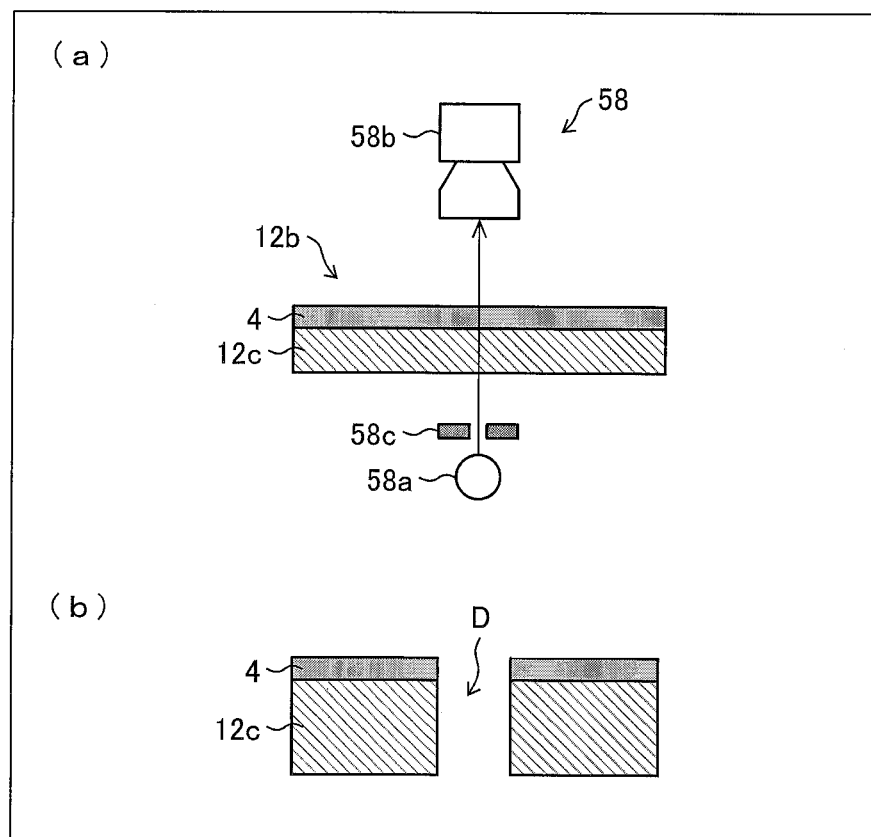
FIG. 7 provides diagrams illustrating a configuration of a pinhole defect inspecting device in the defect detecting step.

FIG. 4 provides diagrams schematically illustrating a defect detecting step and a defect information recording step both included in a method for marking a defect in the heat-resistant separator original sheet 12b. (a) of FIG. 4 is an elevational view of the two steps, whereas (b) of FIG. 4 is a plan view of the two steps. FIG. 5 provides diagrams illustrating a configuration of a base material defect inspecting device 55 in the defect detecting step. FIG. 6 provides diagrams illustrating a configuration of a coating defect inspecting device 57 in the defect detecting step. FIG. 7 provides diagrams illustrating a configuration of a pinhole defect inspecting device 58 in the defect detecting step.

A heat-resistant layer is formed on a separator original sheet 12c by the coating section 54 so that a heat-resistant separator original sheet 12b is prepared. The heat-resistant separator original sheet 12b is wound up around a core 53. Specifically, a base material inspecting step (defect detecting step) is a step of inspecting the separator original sheet 12c for a defect D. The base material inspecting step is carried out by a base material defect inspecting device 55 (defect detecting section, separator producing apparatus) between a step of unreeling the separator original sheet 12c and the coating step. The base material defect inspecting device 55 includes a light source 55a and a detector 55b that are so positioned as to sandwich the separator original sheet 12c. The light source 55a emits light in a direction perpendicular to the front and back surfaces of the separator original sheet 12c, whereas the detector 55b detects light having passed through the separator original sheet 12c. This allows the base material defect inspecting device 55 to inspect the separator original sheet 12c for a defect D present therein, that is, specify the position of a defect D (defect detecting step). The defect D present in the separator original sheet 12c is, for example, a through hole (pinhole), an inappropriate film thickness, or a defect caused by a foreign substance.

A coating inspecting step (defect detecting step) is a step of inspecting the heat-resistant layer 4, formed on the separator original sheet 12c, for a defect D. The coating inspecting step is carried out by a coating defect inspecting device 57 (defect detecting section, separator producing apparatus) between the coating step and a step of winding up the heat-resistant separator original sheet 12b around the core 53. The coating defect inspecting device 57 includes a light source 57a and a detector 57b that are positioned on the side of the heat-resistant layer 4 of the heat-resistant separator original sheet 12b. The light source 57a emits light to the heat-resistant layer 4, whereas the detector 57b detects light having been reflected by the heat-resistant layer 4. This allows the coating defect inspecting device 57 to detect a defect D present in the heat-resistant layer 4 (that is, specify the position of a defect D). The defect D present in the heat-resistant layer 4 is, for example, a crease, peeling off, repellency, and a surface failure. The repellency refers to a defect of a foreign substance, oil, or the like on the surface of the separator original sheet 12c repelling the coating solution from the surface, with the result of local absence of a heat-resistant layer 4 or local formation of an extremely thin heat-resistant layer 4. The surface failure refers to a failure in the thickness of the heat-resistant layer 4.

A pinhole inspecting step (defect detecting step) is a step of inspecting the heat-resistant separator original sheet 12b for a defect D in the form of a pinhole. The pinhole inspecting step is carried out by a pinhole defect inspecting device 58 (defect detecting section, separator producing apparatus) positioned between the coating defect inspecting device 57 and a defect information recording device 56. The pinhole defect inspecting device 58 includes a light source 58a, a detector 58b, and a slit 58c. The light source 58a is positioned on the side of the separator original sheet 12c of the heat-resistant separator original sheet 12b, and emits light in a direction perpendicular to the front and back surfaces of the heat-resistant separator original sheet 12b. The slit 58c lets the light pass therethrough and travel toward the heat-resistant separator original sheet 12b. The detector 58b detects a defect D (that is, specifies the position of a defect D) on the basis of light having passed through the heat-resistant separator original sheet 12b. The defect D in the form of a pinhole has a diameter ranging from several hundreds of micrometers to several millimeters.

The production process involves a defect information recording device 56 positioned between the pinhole defect inspecting device 58 and the core 53. The defect information recording device 56 records, on the heat-resistant separator original sheet 12b, a defect code DC indicative of defect information such as information on the position of any defect D detected by the base material defect inspecting device 55, the coating defect inspecting device 57, or the pinhole defect inspecting device 58. The defect information recording device 56 records such a defect code DC at a portion on a widthwise side of the heat-resistant separator original sheet 12b which portion corresponds to the lengthwise position of the defect D on the heat-resistant separator original sheet 12b. The defect code DC may be code data such as a two-dimensional code or QR Code (registered trademark). The information on the position indicates where the defect D is positioned in the longitudinal and width directions of the heat-resistant separator original sheet 12b. The information on the position may include information with which the type of the defect D is distinguishable. The type of a defect D is, for example, (i) a structural defect in the base material for which defect the base material defect inspecting device 55 inspects the separator original sheet 12c, (ii) a defect caused in the applying step for which defect the coating defect inspecting device 57 inspects the heat-resistant layer 4, or (iii) a defect in the form of an opening for which defect the pinhole defect inspecting device 58 inspects the heat-resistant separator original sheet 12b.

The separator original sheet 12c or heat-resistant separator original sheet 12b is subjected to a film tension of typically not more than 200 N/m, preferably not more than 120 N/m. The term "film tension" refers to a tension applied to a film being conveyed, the tension being applied in the conveying direction over a unit widthwise length of the film. For instance, with a film tension of 200 N/m, a force of 200 N is applied to the film over a width of 1 m. A film tension of more than 200 N/m may form a wrinkle in the conveying direction of the film and decrease the accuracy of defect inspection. The film tension is typically not less than 10 N/m, preferably not less than 30 N/m. A film tension of less than 10 N/m may cause slack in the film or let the film meander. The separator original sheet 12c or heat-resistant separator original sheet 12b has pores P, and is subjected to a film tension lower than a film tension applied to a non-porous film such as an optical film. The separator original sheet 12c or heat-resistant separator original sheet 12b thus has a physical property of being stretchable more easily than a non-porous film such as an optical film. As such, in a case where a defect code DC is recorded at a portion on a widthwise side of the heat-resistant separator original sheet 12b which portion corresponds to the lengthwise position of the defect D on the heat-resistant separator original sheet 12b, the lengthwise position of the defect D is substantially not displaced from the lengthwise position of the defect code DC even in a case where the heat-resistant separator original sheet 12b has been stretched lengthwise. The lengthwise position of a defect D is thus easily specifiable even in the case where the heat-resistant separator original sheet 12b has been stretched lengthwise.

The heat-resistant separator original sheet 12b with a defect code DC recorded at a portion on a widthwise side thereof is wound up around the core 53. The core 53, around which the heat-resistant separator original sheet 12b has been wound up, is carried to a position for the subsequent slitting step.

The defect information recording device 56 (see FIG. 4) records a defect code DC indicative of information on the position of a defect D at a portion on a widthwise side of the heat-resistant separator original sheet 12b which portion corresponds to the lengthwise position of the defect D on the heat-resistant separator original sheet 12b. A defect D is separated from its corresponding defect code DC by a lengthwise distance $L_{MD}$ of, for example, preferably not more than 100 mm, more preferably not more than 30 mm. The defect code DC is separated from a widthwise side of the heat-resistant separator original sheet 12b by a distance $L_{TD}$ of, for example, preferably not more than 100 mm, more preferably not more than 30 mm. The distance $L_{TD}$ is preferably not less than 10 mm because the widthwise sides of the heat-resistant separator original sheet 12b easily become wavy.

<Slitting Apparatus>

The heat-resistant separator 12a (hereinafter referred to as "separator"), produced from the heat-resistant separator original sheet 12b (hereinafter referred to as "separator original sheet"), or the separator 12, produced from the separator original sheet 12c, has a width (hereinafter referred to as "product width") suitable for application products such as the lithium-ion secondary battery 1. For improved productivity, however, the separator original sheet is produced so as to have a width that is equal to or larger than a product width. Then, after having been once produced so as to have a width equal to or larger than the product width, the separator original sheet is cut (slit) into a separator(s) having the product width.

Note that the expression "width of a/the separator" means a dimension of the separator in a direction that is parallel to a plane in which the separator extends and that is perpendicular to the longitudinal direction of the separator. Moreover, "slit" means to cut off a separator original sheet lengthwise (i.e., in a direction in which a film flows in production, MD: machine direction), whereas "cut" means to cut the separator original sheet or separator in a transverse direction (TD). The transverse direction (TD) means a direction (widthwise direction) that is substantially perpendicular to the lengthwise direction (MD) and the thickness direction of the separator.

Figure 8:
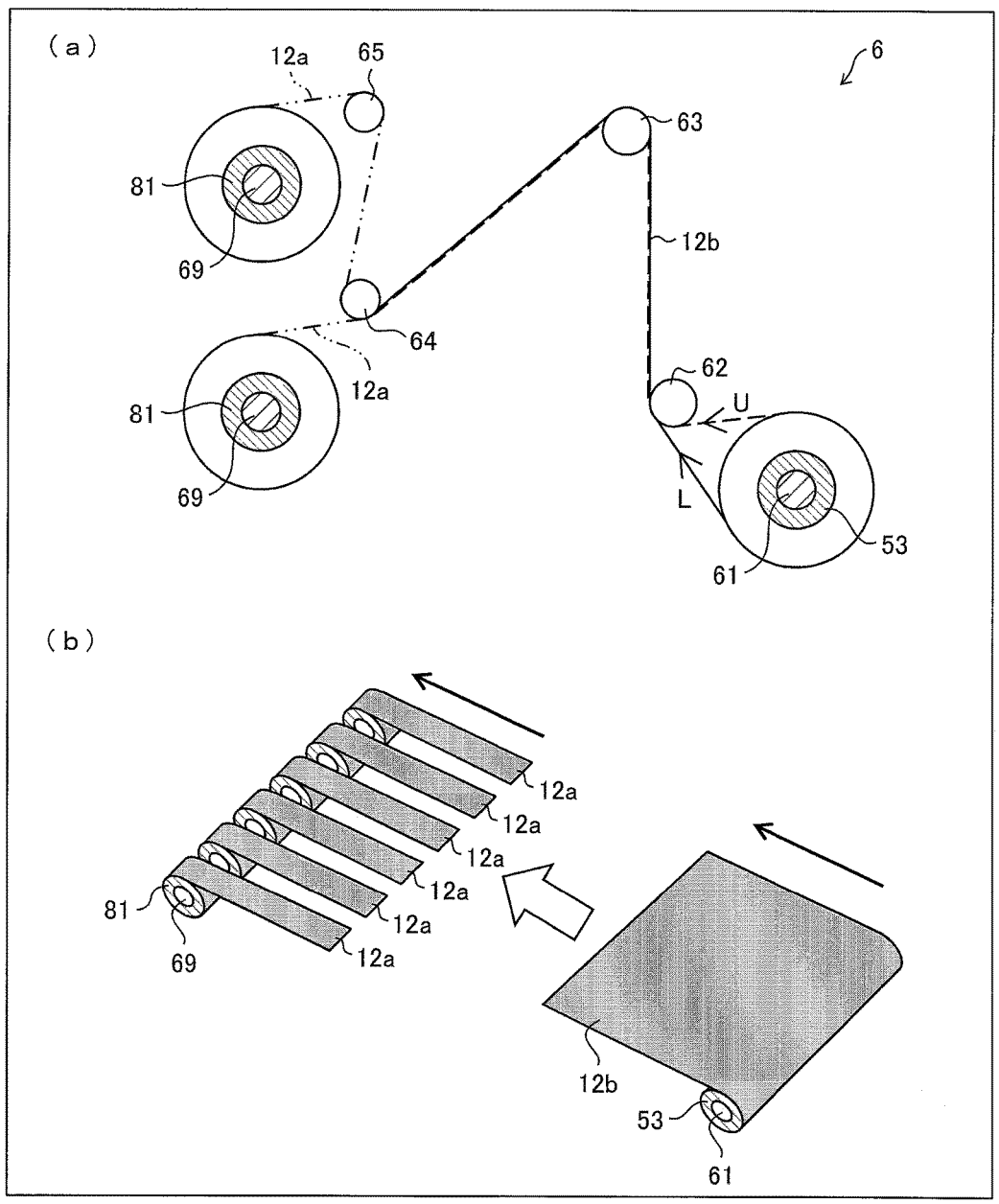
FIG. 8 provides diagrams schematically illustrating a configuration of a slitting apparatus configured to slit a separator.

FIG. 8 provides diagrams schematically illustrating a configuration of a slitting apparatus 6 configured to slit the separator original sheet 12b. (a) of FIG. 8 illustrates the entire configuration, and (b) of FIG. 8 illustrates an arrangement before and after slitting the separator original sheet 12b.

As illustrated in (a) of FIG. 8, the slitting apparatus 6 includes a rotatably supported cylindrical wind-off roller 61, rollers 62 to 65, and wind-up rollers 69. The slitting apparatus 6 is further provided with a cutting device 7 (see FIG. 9) described later.

<Before Slitting>

In the slitting apparatus 6, a cylindrical core 53 on which the separator original sheet 12b is wrapped is fit on the wind-off roller 61. As illustrated in (a) of FIG. 8, the separator original sheet 12b is wound off from the core 53 to a route U or L. The separator original sheet 12b thus wound off is conveyed to the roller 64 via the roller 63 at a speed of, for example, 100 m/min. In the conveying step, the separator original sheet 12b is slit lengthwise into a plurality of separators 12a.

<After Slitting>

As illustrated in (a) of FIG. 8, one or more of the plurality of separators 12a are wound up around respective cores 81 (bobbins) fit on the plurality of wind-up rollers 69. Further, another one or more of the plurality of separators 12a are wound up around respective cores 81 (bobbins) fit on the plurality of wind-up rollers 69. Note that each of the slit separators wound into a roll form is referred to as a "separator roll (film roll)".

<Cutting Device>

Figure 9:
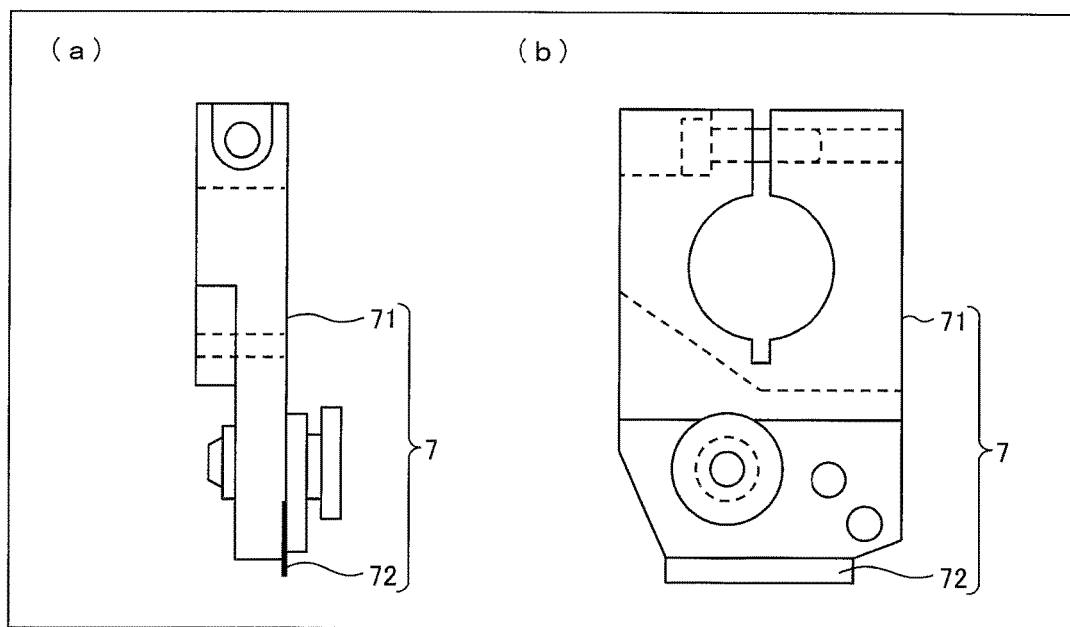
FIG. 9 provides an enlarged view, a side view, and an elevational view of a cutting device included in the slitting apparatus illustrated in FIG. 8.

FIG. 9 provides views each illustrating a configuration of the cutting device 7 (slitting section) of the slitting apparatus 6 illustrated in (a) of FIG. 8. (a) of FIG. 9 is a side view of the cutting device 7, and (b) of FIG. 9 is a front view of the cutting device 7.

As illustrated in (a) and (b) of FIG. 9, the cutting device 7 includes a holder 71 and a blade 72. The holder 71 is fixed to a housing or the like provided in the slitting apparatus 6. The holder 71 holds the blade 72 in such a manner that the blade 72 and the separator original sheet 12b being conveyed have a fixed positional relation. The blade 72 has a finely sharpened edge and slits the separator original sheet by using this edge.

Figure 10:
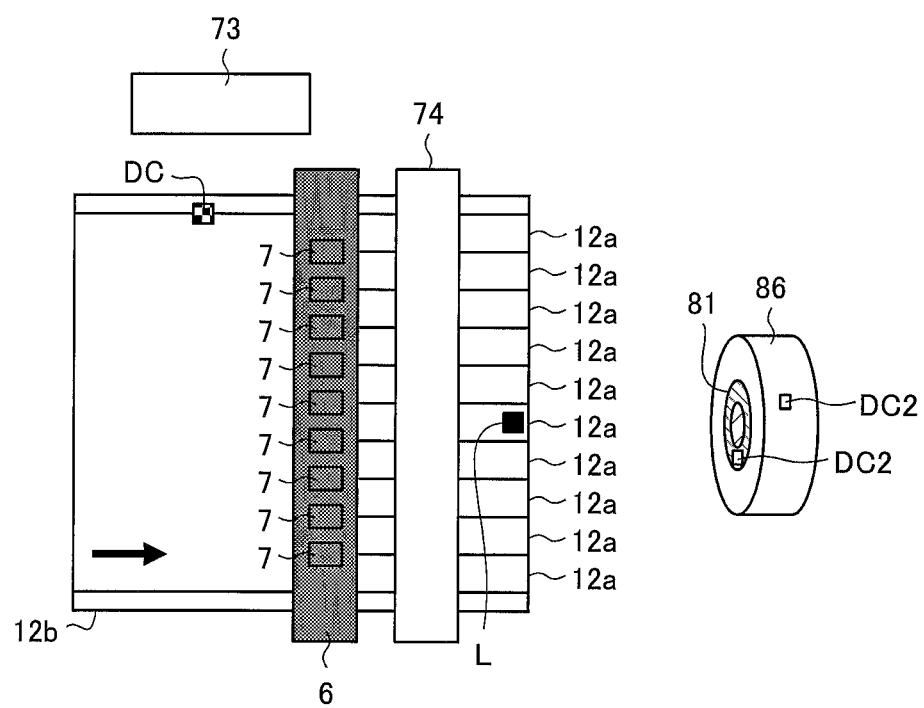
FIG. 10 is a diagram schematically illustrating a reading step, a mark providing step, and a wind-up step all included in a method for specifying the position of a defect in a separator.

FIG. 10 is a diagram schematically illustrating a reading step (defect information obtaining step), a determining step, a mark providing step, and a wind-up step all included in a method for specifying the position of a defect in a separator 12a. The separator original sheet 12b is wound off from the core 53 (see FIG. 8) at a fixed speed (for example, 80 m/min). The reading section 73 (defect information obtaining section) reads a defect code DC recorded at a portion on a widthwise side of the separator original sheet 12b to obtain defect information (original sheet defect position information) for the separator original sheet 12b (defect information obtaining step, original sheet defect information obtaining step). The plurality of cutting devices 7, included in the slitting apparatus 6, cut the separator original sheet 12b lengthwise to prepare a plurality of separators 12a (slitting step).

<Defect Removing Step>

Next, a determining device 75 (determining section) determines on the basis of the defect code DC read by the reading section 73 that a separator among the plurality of separators which separator has the defect D is defective (determining step). A mark providing device 74 then provides a single mark L at a position corresponding to the defect D in the separator 12a, which is defective as the determining device 75 has determined (defect marking providing step). In a case where there are a plurality of defects D present, the determining device 75 determines that a plurality of separators 12a are defective. The mark L is preferably a label, so the mark providing device 74 is preferably a labeler.

The mark L may be, instead of a label, a mark drawn with a pen or a mark applied by an injector. The mark L may also be a thermolabel, which is printed by heating the separator 12a (made of resin). The mark L may also be provided by forming a hole in the separator 12a with use of a laser.

The plurality of separators 12a, prepared by slitting the separator original sheet 12b with use of the cutting devices 7, are each wound up around one of a plurality of cores 81 (wind-up step).

The mark providing device 74 then records information on the position of the defect D in the lengthwise direction of the separator original sheet 12b, which defect D is indicated by a defect code DC. The mark providing device 74 records such information as a defect code DC2 on (i) an outermost portion 86 of the separator 12a identified and wound up and/or (ii) the core 81.

Figure 11:
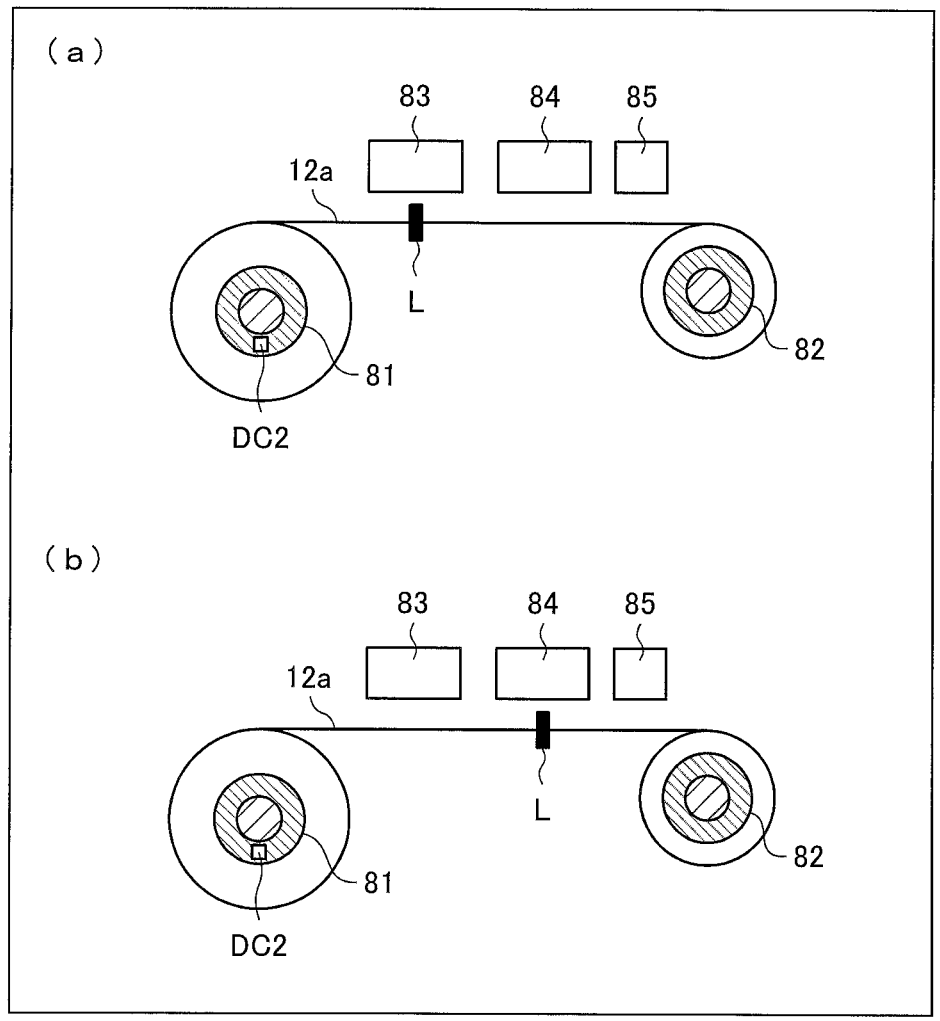
FIG. 11 provides diagrams schematically illustrating a mark sensing step and a defect removing step both included in a method for specifying the position of a defect in a separator.

FIG. 11 provides diagrams schematically illustrating a mark sensing step and a defect removing step both included in a method for specifying the position of a defect in a separator 12a. (a) of FIG. 11 is a diagram schematically illustrating the mark sensing step. (b) of FIG. 11 is a diagram schematically illustrating the defect removing step. First, a mark sensing device 83 reads a defect code DC2 recorded on the outermost portion 86 and/or core 81. The mark providing device 74 receives information read by the mark sensing device 83 and attaches a mark L to the separator 12a with the defect D present therein. The mark sensing step then starts an operation of winding off the separator 12a from the core 81 and winding up the heat-resistant separator 12a again around a core 82. Next, the mark sensing device 83, on the basis of information on the position of the defect D (indicated by the defect code DC2 read by the mark sensing device 83) in the lengthwise direction of the separator original sheet 12b, slows the above operation when the defect D has become close to the core 82.

The mark sensing device 83 then senses the mark L, which is attached to the position corresponding to the defect D in the separator 12a (mark sensing step). When the mark sensing device 83 has sensed the mark L, the mark sensing device 83 stops the operation of winding up the separator 12a again. Then, a defect removing device 84 cuts the separator 12a widthwise at (i) a position upstream of the defect D (which corresponds to the mark L) and (ii) a position downstream of the defect D, and removes the defect D from the separator 12a (defect removing step). The defect removing step may alternatively be carried out manually by an operator instead of the defect removing device 84. Then, a connecting device 85 connects two portions of the separator 12a that are separated from each other as the result of cutting the separator 12a (connecting step). The connecting step may alternatively be carried out manually by an operator instead of the connecting device 85. Next, the connecting device 85 resumes the operation of winding up the separator 12a again. The operation of winding off the separator 12a from the core 81 and winding up the separator 12a again around the core 82 is then completed. The two portions of the separator 12a, which result from dividing the separator 12a, may alternatively be left unconnected to be individually wound up around separate cores. In other words, the separator 12a may be wound up again in such a manner that that portion of the separator 12a which is downstream of the removed portion is wound up around the core 82, whereas that portion of the separator 12a which is upstream of the removed portion is wound up around another core.

Embodiment 2

Embodiment 1 is an example in which information on the position of a defect D present in a separator original sheet 12b is recorded at a widthwise end of the separator original sheet 12b. The present invention is, however, not limited to such a configuration, and may be configured such that information on the position of a defect D is recorded in an information storing device.

Figure 12:
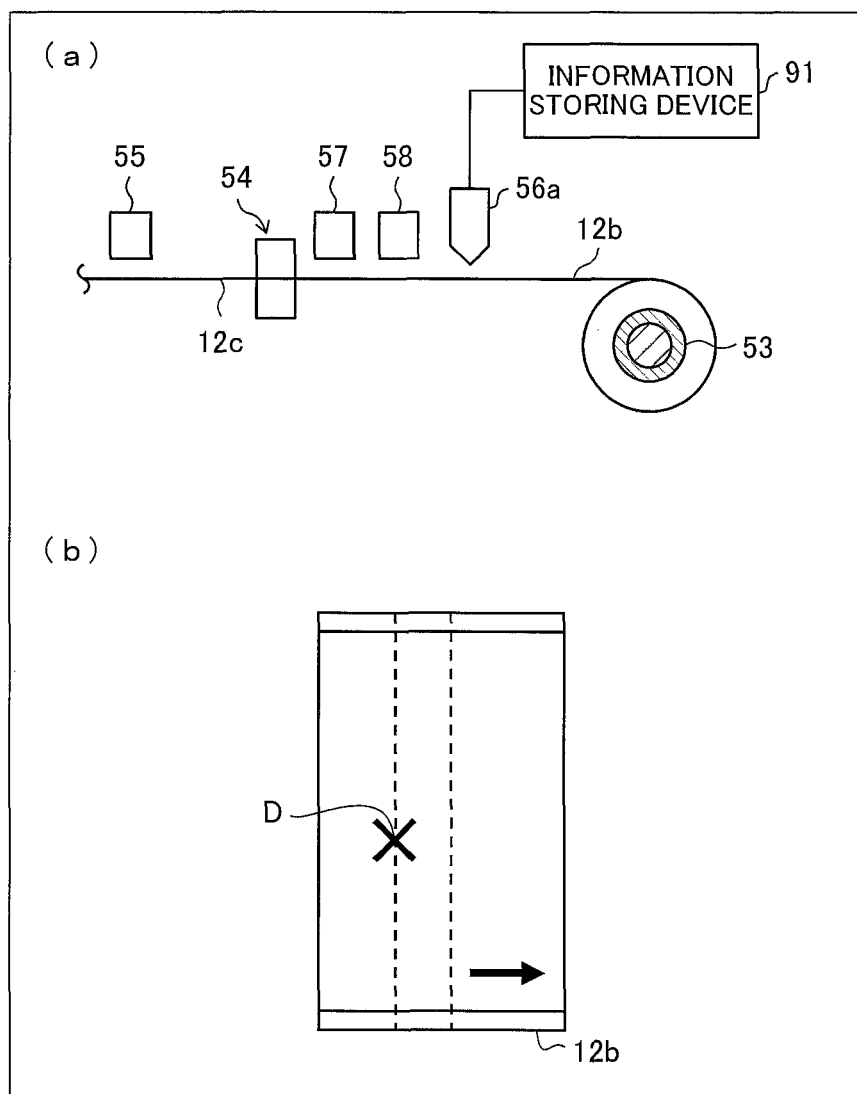
FIG. 12 provides diagrams schematically illustrating a defect detecting step and a defect information recording step both included in a method in accordance with Embodiment 2 for marking a defect in a separator original sheet.
Figure 13:
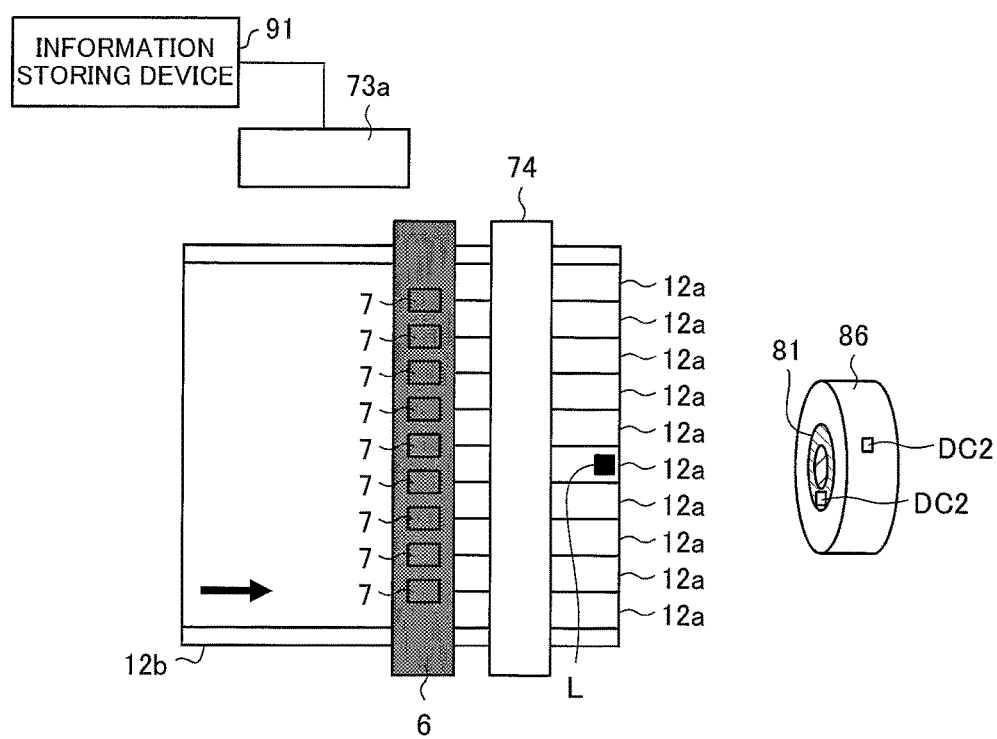
FIG. 13 is a diagram schematically illustrating a reading step, a mark providing step, and a wind-up step all included in a method for specifying the position of a defect in a separator.

FIG. 12 provides diagrams schematically illustrating a defect detecting step and a defect information recording step both included in a method in accordance with Embodiment 2 for marking a defect in a separator original sheet 12b. FIG. 13 is a diagram schematically illustrating a reading step, a mark attaching step, and a wind-up step all included in a method for specifying the position of a defect in a separator 12a. Any constituent element of Embodiment 2 that is identical to a corresponding constituent element described earlier for Embodiment 1 is assigned a common reference sign, and is not described in detail here.

A defect information recording device 56a (defect information recording section, separator original sheet producing apparatus) records, in an information storing device 91, positional information indicative of the lengthwise and widthwise positions of a defect D that is present in the separator original sheet 12c or 12b and that has been detected by the base material defect inspecting device 55, the coating defect inspecting device 57, or the pinhole defect inspecting device 58. A reading section 73a reads the positional information from the information storing device 91 (reading step).

Embodiment 3

Figure 14:
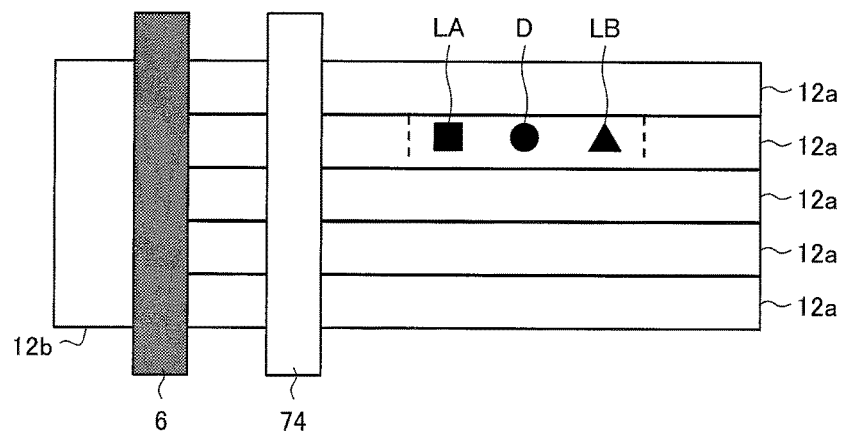
FIG. 14 a diagram illustrating a separator provided with marks during a mark providing step after a slitting step of a separator producing method in accordance with Embodiment 3.
Figure 15:
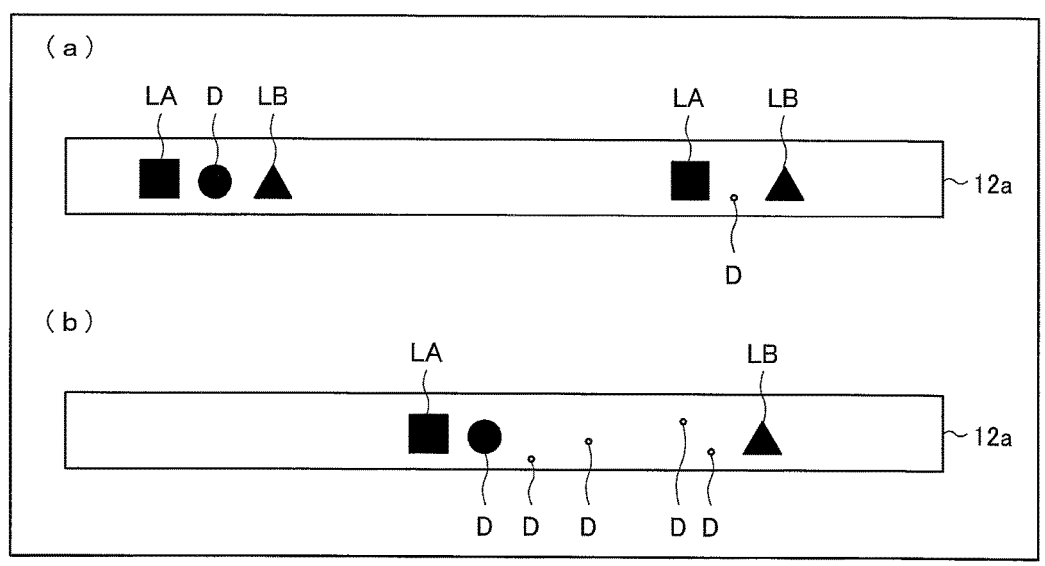
FIG. 15 provides diagrams each illustrating a positional relation between defects in a separator and marks.

The following description will discuss another embodiment of the present invention with reference to FIGS. 14 and 15. Note that, for convenience of explanation, identical reference numerals are given to members which have respective functions identical with those described in Embodiment 1 or 2, and descriptions of the respective members are omitted.

In Embodiment 1, the mark providing device 74 provides a single mark L at a position corresponding to a defect D in a separator 12a. How the mark providing device 74 provides a mark L is, however, not limited to that. The following description will discuss how a mark providing device 74 (defect marking providing section) of Embodiment 3 provides a mark L.

FIG. 14 is a diagram illustrating a separator provided with marks during a mark providing step after the slitting step. FIG. 14 shows a quadrangle to indicate a mark LA and a triangle to indicate a mark LB for convenience of description. The respective shapes of the marks LA and LB are, however, not limited to any particular ones. The marks LA and LB may have an identical shape (or color) or respective shapes (or colors) different from each other.

As illustrated in FIG. 14, the separator mark providing device 74 of Embodiment 3 provides marks LA and LB (markings) indicative of the position of a defect D at respective positions in the vicinity of the defect D (defect marking providing step). In particular, the mark providing device 74 preferably provides (i) a mark LA at a position on a first side of the defect D in the longitudinal direction of the separator 12a and (ii) a mark LB at a position on a second side of the defect D in the longitudinal direction of the separator 12a so that the defect D is positioned between the pair of the marks LA and LB. The mark providing device 74 may alternatively further provide one or more marks in the vicinity of a single defect D in addition to a pair of marks LA and LB (that is, a total of three or more marks).

A separator 12a provided with marks LA and LB at respective positions in the vicinity of a defect D as described above accurately shows the area of the defect D. In particular, a separator 12a provided with a mark LA at a position on a first lengthwise side of a defect D and a mark LB at a position on a second lengthwise side of the defect D accurately shows the lengthwise area of the defect D.

With the above arrangement, cutting the separator 12a widthwise along two cutting lines (see the broken lines in FIG. 14) with the marks LA and LB in-between during a defect removing step makes it possible to cut off a portion of the separator 12a which portion has a length that covers the entire lengthwise area of the defect D, thereby reliably removing the defect D. This in turn makes it possible to prevent a separator 12a having a defect D (defective separator) from being made publicly available.

FIG. 15 provides diagrams each illustrating a positional relation between defects in a separator and marks. (a) of FIG. 15 is a diagram illustrating a separator having two defects. (b) of FIG. 15 is a diagram illustrating a separator having two or more defects close to one another.

As illustrated in (a) of FIG. 15, a method for producing a separator 12a which method includes the mark providing step of Embodiment 3 makes it possible to accurately show the area of a defect D in a separator 12a even in a case where that defect D is too small for an operator to visually recognize.

Further, as illustrated in (b) of FIG. 15, in a case where a separator 12a has a plurality of defects D close to one another and apart from one another by small distances in the longitudinal direction of the separator 12a, the mark providing device 74 may provide a mark LA (first marking) at a position on a first lengthwise side (hereinafter referred to as upstream) of that defect D which is positioned most upstream and a mark LB (second marking) at a position on a second lengthwise side (hereinafter referred to as downstream) of that defect D which is positioned most downstream. This configuration makes it possible to show the range of a group of defects D with use of a pair of marks LA and LB, thereby reducing the number of marks to be provided.

In a case where a separator 12a has a plurality of defects D that are apart from each other in the longitudinal direction of the separator 12a by a small distance, removing the plurality of defects D from the separator 12a produces a short cutoff of the separator 12a which cutoff corresponds to a region between the plurality of defects D.

Thus, in a case where a separator 12a has a plurality of defects D that are apart from each other in the longitudinal direction of the separator 12a by a distance that is less than a predetermined value so that removing the plurality of defects D from the separator 12a fails to produce, from the region between the plurality of defects D, a cutoff of the separator 12a which cutoff has a length of not less than an intended, predetermined value (for example, 100 m as a product standard), the mark providing device 74 preferably provides a pair of marks LA and LB so that the plurality of defects D as a defect group are all positioned between the pair of the marks LA and LB as illustrated in (b) of FIG. 15.

The above arrangement makes it possible to, in a case where a separator 12a is cut on the basis of marks LA and LB, (i) reduce the number of cutting operations that result in a separator 12a having a length that is less than a predetermined value and (ii) reduce the number of cutting operations necessary to produce a separator 12a having no defect and a length that is not less than the predetermined value.

Embodiment 4

Figure 16:
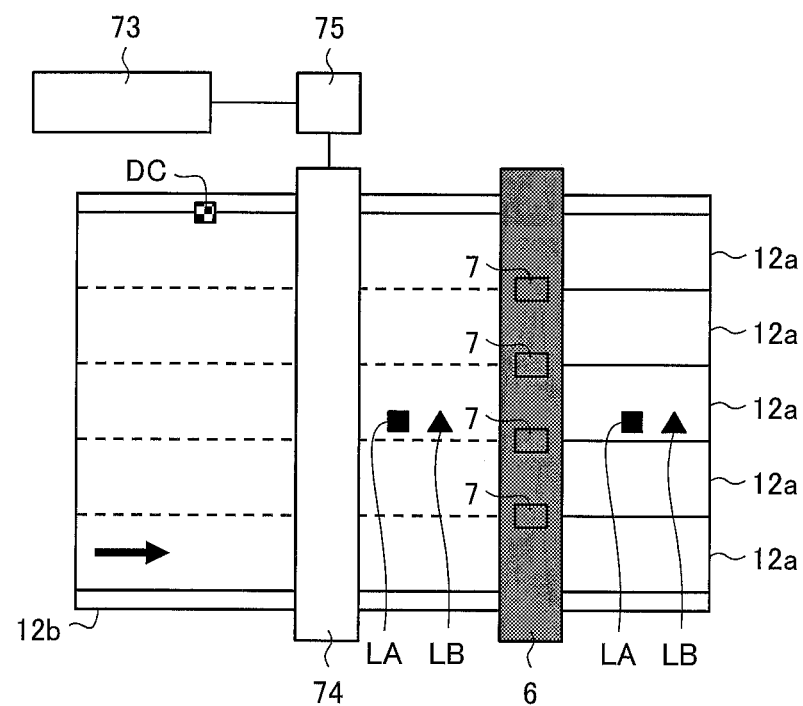
FIG. 16 is a diagram schematically illustrating a reading step, a mark providing step, and a wind-up step all included in a separator producing method in accordance with Embodiment 4.

The following description will discuss another embodiment of the present invention with reference to FIG. 16. Note that, for convenience of explanation, identical reference numerals are given to members which have respective functions identical with those described in Embodiment 1, 2, or 3, and descriptions of the respective members are omitted.

FIG. 16 is a diagram schematically illustrating a reading step, a mark providing step, and a wind-up step all included in a method for specifying the position of a defect in a separator 12a.

The production method of Embodiment 3 includes a slitting step and a mark providing step successively. These steps are, however, not necessarily carried out in that order. A production method of Embodiment 4 differs from the production method of Embodiment 3 in that the former includes a mark providing step and a slitting step in that order. The following description will discuss Embodiment 4 in greater detail.

As illustrated in FIG. 16, Embodiment 4 is configured such that (i) a reading section 73 reads a defect code DC to obtain information (original sheet defect position information) on the position of a defect D in a separator original sheet 12b (defect information obtaining step) and (ii) a mark providing device 74 provides marks LA and LB to the separator original sheet 12b on the basis of the information on the position of the defect D in the separator original sheet 12b (defect marking providing step). The slitting apparatus 6 then slits the separator original sheet 12b, to which the marks LA and LB have been provided.

In a case where a mark L is provided to a separator 12a after the slitting step on the basis of information on the position of a defect D in the separator original sheet 12b, widthwise displacement of separators 12a during the slitting step may prevent the position of the defect D in the separator original sheet 12b from corresponding to the position of the defect D in a separator 12a after the slitting step. A mark L provided for a defect D may thus be displaced. In contrast, providing a mark L to a separator original sheet 12b before the slitting step on the basis of information on the position of a defect D in the separator original sheet 12b ensures that the mark L is correctly positioned to correspond to the defect D.

The marks LA and LB are preferably each so provided as not to overlap a slit line. This makes it possible to prevent a situation in which marks LA and LB have been cut during the slitting step and it is consequently difficult to determine whether a separator is defective.

Embodiment 5

Figure 17:
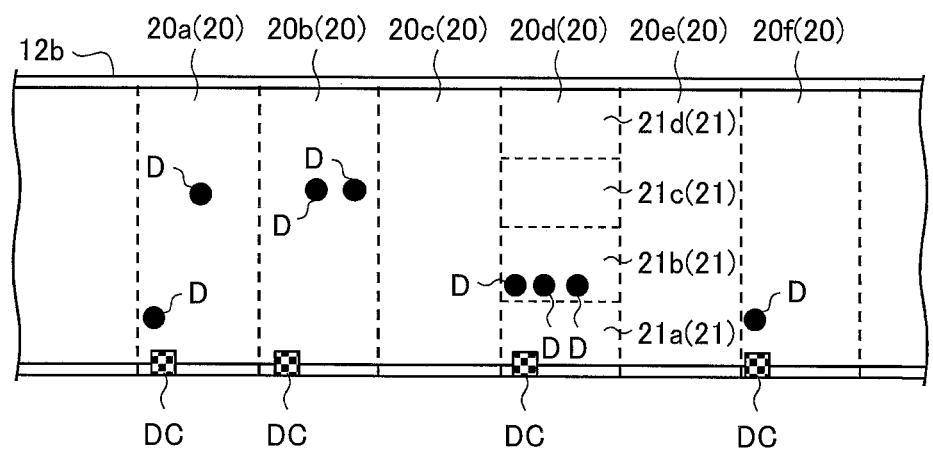
FIG. 17 is a plan view of a separator original sheet for illustration of where a defect code is recorded in a separator producing method in accordance with Embodiment 5.
Figure 18:
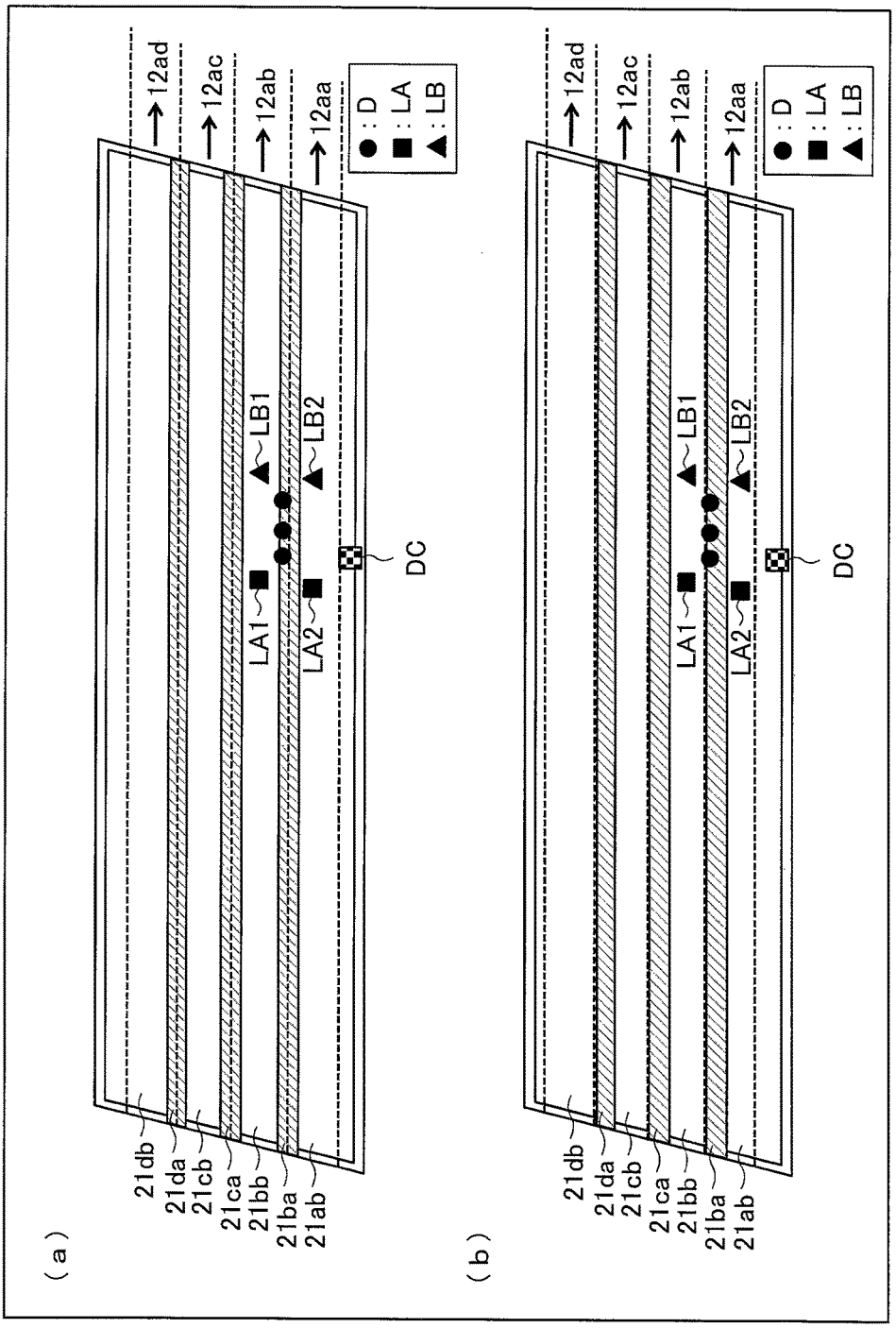
FIG. 18 provides perspective views of a separator original sheet provided with marks at a position corresponding to defects.
Figure 19:
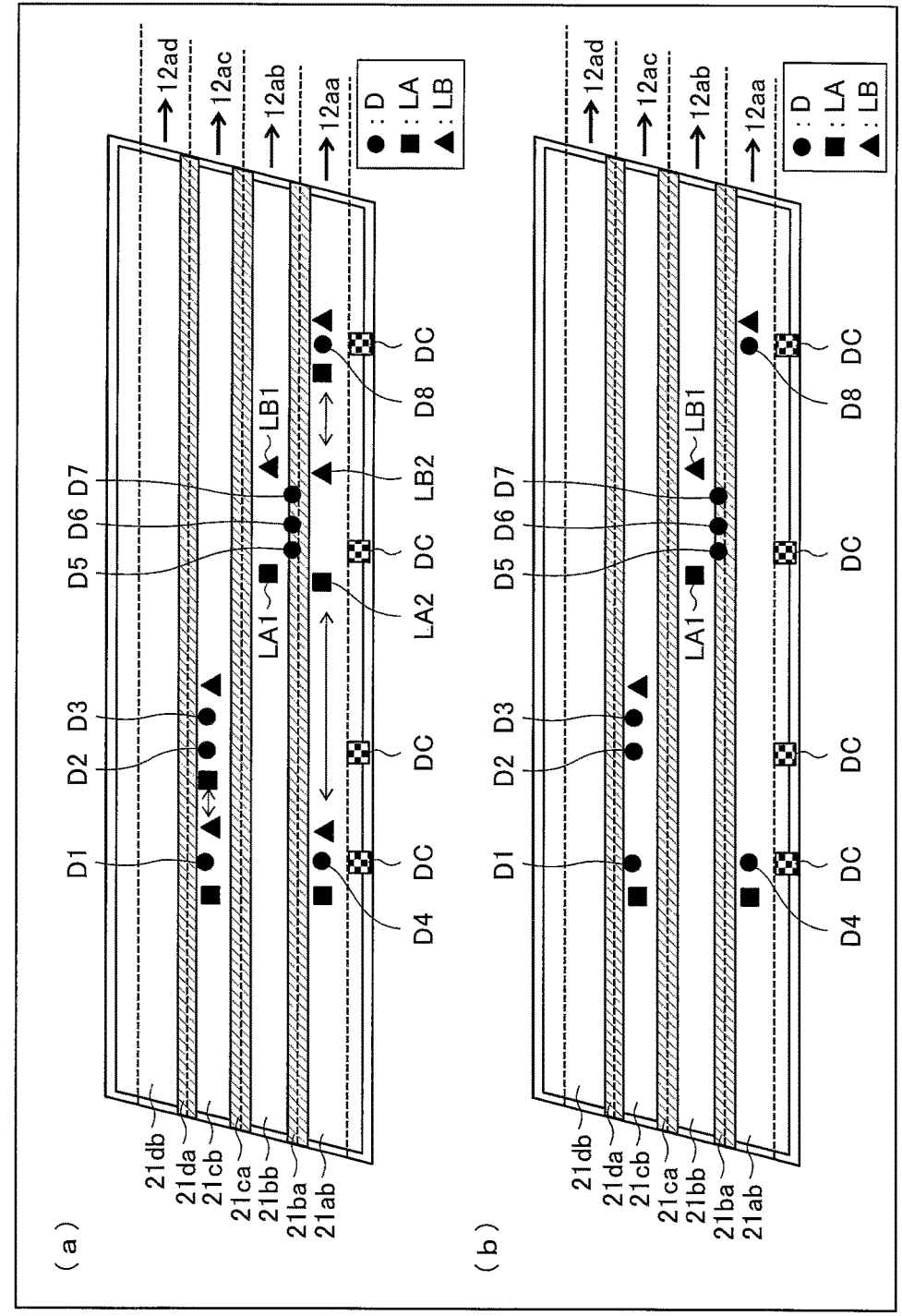
FIG. 19 provides perspective views of a separator original sheet provided with marks at a position corresponding to defects.

The following description will discuss another embodiment of the present invention with reference to FIGS. 17 to 19. Note that, for convenience of explanation, identical reference numerals are given to members which have respective functions identical with those described in Embodiment 1, 2, 3, or 4, and descriptions of the respective members are omitted.

In Embodiment 1, the defect information recording device 56 records a defect code DC at a portion of a separator original sheet 12b which portion corresponds to the position of a defect D in the longitudinal direction of the separator original sheet 12b. The defect information recording device 56, however, does not necessarily record a defect code DC in such a manner.

The following description will discuss how the defect information recording device 56 of Embodiment 3 records a defect code DC.

<Unit Region>

FIG. 17 is a plan view of a separator original sheet for illustration of where a defect code DC is recorded. As illustrated in FIG. 17, the defect information recording device 56 of Embodiment 5 records (forms), for each unit region 20 having a predetermined length in the longitudinal direction of the separator original sheet 12b, a defect code DC indicative of any defect D in that unit region 20 (defect information recording step). The unit region 20 can have a length of, for example, 250 mm in the longitudinal direction of the separator original sheet 12b.

FIG. 17 shows six example unit regions 20a to 20f arranged in the longitudinal direction of the separator original sheet 12b. FIG. 17 also shows a defect code DC recorded in correspondence with each of the unit regions 20a, 20b, 20d, and 20f, each of which includes one or more defects D. FIG. 17 shows an example in which the defect information recording device 56 does not record a defect code DC in a unit region 20 having no defect D such as the unit regions 20c and 20e.

The defect information recording device 56 records, in a unit region 20 having a plurality of defects D such as the unit regions 20a and 20b, a single defect code DC indicative of, for example, information on the respective positions of the plurality of defects D.

A reading section 73 reads a defect code DC indicative of, for example, information on the respective positions of a plurality of defects D for each unit region 20 to obtain defect information (defect information obtaining step). Then, a mark providing device 74 provides a pair of marks LA and LB on the respective upstream and downstream sides of a unit region 20 having a defect D in the longitudinal direction of the separator 12a (or separator original sheet 12b before the slitting step) so that the unit region 20 having the defect D is positioned between the pair of the marks LA and LB (defect marking providing step).

Recording, in each unit region 20, a single defect code DC indicative of, for example, information on the respective positions of a plurality of defects D and providing a pair of marks LA and LB so that a unit region 20 having a defect D is positioned between the pair of the marks LA and LB as described above makes it possible to reduce the number of recorded defect codes DC and the number of marks L. This in turn makes it possible to simplify the production process.

<Information Included in Defect Code>

The defect information recording device 56 records a defect code DC indicative of detailed information such as (i) the number and/or type(s) of defects D in the unit region 20, (ii) the coordinates of the position of each defect D on the surface of the separator original sheet 12b, and (iii) the size of each defect D.

However, in a case where there are many defects D in a unit region 20, a single defect code DC cannot include detailed information on all of those defects D. The defect information recording device 56 may thus alternatively be configured to divide a unit region 20 into a plurality of divisional regions 21 arranged in the width direction of the separator original sheet 12b and record a defect code DC indicative of simple information such as whether there is any defect D in each divisional region 21.

For example, as illustrated in FIG. 17 as an example, the defect information recording device 56 divides the unit region 20d, which has three defects D, into divisional regions 21a to 21d arranged in the width direction of the separator original sheet 12b and records a defect code DC indicative of information on whether there is any defect D in each of the divisional regions 21a to 21d. Specifically, the defect information recording device 56 records a defect code DC indicative of the following simple information: The divisional region 21a has no defect D. The divisional region 21b has defects D. The divisional region 21c has no defect D. The divisional region 21d has no defect D.

The above configuration makes it possible to reduce the amount of information to be included in a defect code DC. The divisional regions 21 illustrated in FIG. 17 are a mere example. The number of divisional regions 21 arranged in the width direction of a separator original sheet 12b and the width of each divisional region 21 can be set as appropriate.

The defect information recording device 56 may alternatively be configured to switch between a first mode, in which it records a defect code DC indicative of detailed information, and a second mode, in which it records a defect code DC indicative of simple information, in correspondence with the number of defects D in the unit region 20. The above configuration makes it possible to, in a case where there is a restriction on the amount of information that can be included in a defect code DC, record a defect code DC indicative of information suitable under that restriction.

<Determining Step>

In Embodiment 1, the determining device 75 (determining section) identifies a single defective separator on the basis of a single defect D. A determining device 75 of Embodiment 5 carries out a determining step different from that carried out by the determining device 75 in Embodiment 1 or 2.

Embodiment 5 is configured such that (i) a reading section 73 reads a defect code DC recorded on a separator original sheet 12b, (ii) a slitting apparatus 6 slits the separator original sheet 12b along slit lines extending in the longitudinal direction of the separator original sheet 12b, and (iii) the determining device 75 determines on the basis of a single defect D that a first separator 12a actually having that defect D and a second separator 12a adjacent to the first separator 12a are defective.

Then, a mark providing device 74 provides the first separator 12a (that is, that separator 12a out of the two separators 12a adjacent to each other via a slit line which actually has the defect D) with a pair of marks LA1 and LB1 indicative of the position of the defect D, and also provides a pair of marks LA2 and LB2 at a portion of the second separator 12a which portion corresponds to the marks LA1 and LB1 (defect marking providing step). A later step cuts off a portion of the first separator 12a on the basis of the marks LA1 and LB1 and also cuts off a portion of the second separator 12a on the basis of the marks LA2 and LB2.

In a case where the mark providing step and the slitting step are carried out in that order as in the production method of Embodiment 4, the mark providing device 74 provides marks LA1 and LB1 respectively to those portions of the separator original sheet 12b which correspond to the two separators 12a that have been determined as defective.

With the above arrangement, even in a case where the slitting apparatus 6 has slit a separator original sheet 12b at positions different from desired slit positions, so that a defect D is not present in a first separator 12a in which the defect D would otherwise be present and that the defect D is present in a second separator 12a different from and adjacent to the first separator 12a, it is possible to determine that the second separator 12a is a defective separator 12a and cut off a portion corresponding to the defect D, thereby reducing the possibility of making a separator 12a having a defect D publicly available.

The defect marking providing step may be followed by a step of checking with use of a mark checking device whether the mark providing device 74 has provided a mark L at an appropriate position.

Another example of the production method of Embodiment 5 is arranged such that (i) the reading section 73 reads a defect code DC indicative of simple information on whether each divisional region has one or more defects and that (ii) the determining device 75 determines on the basis of each divisional region 21 having at least one defect D that a first separator 12a including a divisional region 21 having a defect D and a second separator 12a different from and adjacent to the first separator 12a are defective. In this case, the mark providing device 74 provides a pair of marks LA1 and LB1 to each of the two separators 12a (or those portions of the separator original sheet 12b which correspond to the two separators 12a) each of which includes a divisional part of the divisional region 21 having the defect D (defect marking providing step).

The defect removing device 84 may, as illustrated in FIG. 11, cut off a portion of each of the two separators 12a on the basis of the marks L1 and L2 provided to each of the two separators 12a after the slitting step (defect cutoff step).

The following description will discuss Embodiment 5 in greater detail with reference to drawings. The description below deals with a step of, in a case where the defect information recording device 56 has recorded a defect code DC indicative of simple information, the determining device 75 determining that a separator is defective.

FIG. 18 provides perspective views of a separator original sheet provided with marks at a position corresponding to defects. (a) of FIG. 18 shows broken lines to indicate intended slit lines. (b) of FIG. 18 shows broken lines to indicate slit lines displaced from the intended positions.

FIG. 18 shows separator original sheets 12b each of which has been provided with marks LA and LB during the mark providing step and is to be slit during the slitting step (that is, has not been slit yet). The slitting step and the mark providing step may alternatively be carried out in that order as in the production method of Embodiment 3. In such a case, marks LA and LB are provided to a separator 12a after the slitting step.

FIG. 18 shows example separator original sheets 12b each provided with a defect code DC recorded by the defect information recording device 56 to indicate simple information for narrow divisional regions 21ba, 21ca, and 21da and wide divisional regions 21ab, 21bb, 21cb, and 21db arranged alternately.

As illustrated in (a) of FIG. 18, in a case where a narrow divisional region 21ba has defects D, the determining device 75 determines that two separators 12ab and 12aa each including a divisional part of the divisional region 21ba are defective. In other words, the determining device 75 determines in a case where a divisional region through which a slit line extends has a defect D that two separators 12a overlapping with that divisional region are defective. The slitting step may alternatively be a step (not shown) of slitting a separator original sheet along slit lines extending on the boundary lines of the divisional regions to produce separators corresponding to the respective regions defined by the boundary lines of the divisional regions. In such a case, the determining device 75 determines that a separator 12a including a divisional region having a defect D and any separator 12a including a divisional region adjacent to the above divisional region via a slit line are defective.

The mark providing device 74 provides a pair of marks LA1 and LB1 to that portion of the separator original sheet 12b which corresponds to the separator 12ab, which has been determined as defective, and also provides a pair of marks LA2 and LB2 to that portion of the separator original sheet 12 which corresponds to the separator 12aa, which has been determined as defective. The slitting apparatus 6 then slits the separator original sheet 12b, which has been provided with the marks LA1, LB1, LA2, and LB2, along the slit lines indicated by broken lines in FIG. 18. A later step cuts off a portion of the separator 12ab on the basis of the marks LA1 and LB1 and also cuts off a portion of the separator 12aa on the basis of the marks LA2 and LB2.

As illustrated in (a) of FIG. 18, in a case where a separator original sheet 12*b* has been slit along the intended slit lines during the slitting step, the separator 12*ab* will have the defects D. However, as illustrated in (b) of FIG. 18, in a case where a separator original sheet 12*b* has been slit along slit lines displaced from the intended positions, the separator 12*aa* will have the defects D. As described above, the two separators 12*aa* and 12*ab*, each of which includes a divisional part of the divisional region 21*ba* having the defects D, can both have the defects D.

The production method of Embodiment 5 provides not only marks LA1 and LB1 to a portion corresponding to the separator 12*ab*, but also marks LA2 and LB2 to a portion corresponding to the separator 12*aa*. With this arrangement, even in a case where slit lines have been displaced from the intended positions and the separator 12*aa* has defects D as a result, it is possible to prevent a situation in which marks are not provided in correspondence with the defects D in the separator 12*aa*.

Thus, even in a case where slit lines have been displaced from the intended positions and the separator 12*aa* has defects D as a result, since the separator 12*aa* has been provided with marks LA2 and LB2 in the vicinity of a position corresponding to the defects D, it is possible to determine the respective positions of the defects D in the separator 12*aa*. Cutting off a portion of the separator 12*aa* on the basis of the marks LA2 and LB2 can prevent the separator 12*aa* as a defective separator from being made publicly available.

FIG. 19 provides perspective views of a separator original sheet provided with marks at respective positions corresponding to one or more defects. (a) of FIG. 19 illustrates a separator original sheet provided with marks in the vicinity of individual defects. (b) of FIG. 19 illustrates a separator original sheet provided with a pair of marks so that a plurality of defects as a defect group are positioned between the pair of the marks.

As illustrated in (a) of FIG. 19, in a case where a mark LB corresponding to a defect D1 is separated by only a small distance from a mark LA corresponding to defects D2 and D3, removing the defects D1 to D3 from the separator 12*ac* fails to provide a sufficiently long cutoff from the region between the defects D1 and D2.

Further, in a case where a mark LB corresponding to a defect D4 is separated by only a small distance from a mark LA2 corresponding to defects D5 to D7, removing the defect D4 from the separator 12*aa* and also removing a portion corresponding to the defects D5 to D7 in view of the possibility that displacement of the slit positions may result in the defects D5 to D7 being present in the separator 12*aa*, it is impossible to obtain a sufficiently long cutoff from the region between the defect D4 and the portion corresponding to the defects D5 to D7. Similarly, in a case where a mark LB2 corresponding to the defects D5 to D7 is separated by only a small distance from a mark LA corresponding to a defect D8, removing the defect D8 from the separator 12*aa* and also removing a portion corresponding to the defects D5 to D7 in view of the possibility that displacement of the slit positions may result in the defects D5 to D7 being present in the separator 12*aa*, it is impossible to obtain a sufficiently long cutoff from the region between the defect D8 and the portion corresponding to the defects D5 to D7.

Thus, in a case where it is impossible to produce, from the region between the defects D, a cutoff of the separator 12*a* which cutoff has a length of not less than an intended, predetermined value (for example, 100 m), the mark providing device 74 preferably provides a pair of marks LA and LB so that the plurality of defects D as a defect group are all positioned between the pair of the marks LA and LB as illustrated in (b) of FIG. 19. In such a case, the mark providing device 74 preferably provides a pair of marks LA and LB so that assumed defects as the defect group are also all positioned between the pair of the marks LA and LB which assumed defects are for a case where marks are provided at a portion corresponding to the separator 12*aa* in view of displacement of the slit positions as with the defects D5 to D7 for the separator 12*aa*.

With the above arrangement, cutting a separator 12*a* on the basis of marks LA and LB does not produce a cutoff having a length that is less than a predetermined value and makes it possible to produce only a separator 12*a* having no defect and a length that is not less than the predetermined value.

The above description deals with an example with reference to FIGS. 18 and 19 in which example the mark providing step and the slitting step are carried out in that order as in the production method of Embodiment 4. The production method of Embodiment 5 is, however, not limited to that. Specifically, the slitting step and the mark providing step may be carried out in that order as in the production method of Embodiment 3. In such a case, the mark providing device 74 provides marks LA1 and LB1 to the separator 12*ab* and marks LA2 and LB2 to the separator 12*aa* after the slitting step. In a case where marks are provided to a separator original sheet 12*b* before the slitting step, those marks may be cut during the slitting step. However, providing marks LA1 and LB1 and marks LA2 and LB2 respectively to the separators 12*ab* and 12*aa* after the slitting step makes it possible to avoid such a risk.

Other Aspects of the Present Invention

In order to attain the above object, a separator original sheet producing method in accordance with an embodiment of the present invention includes the steps of: forming a separator original sheet; detecting a defect in the separator original sheet; and recording defect information including information on a first position of the defect which first position is a position in a width direction of the separator original sheet. The term "separator original sheet" refers to a wide separator that has not been slit.

The above feature involves recording defect information including information on a first position of a defect which first position is a position in the width direction of a separator original sheet. Referring to information recorded as such makes it possible to easily specify the position of a defect in a separator original sheet. This in turn makes it possible to easily remove a defect in a separator original sheet.

The separator original sheet producing method in accordance with an embodiment of the present invention may preferably be arranged such that the defect information further includes information on a second position of the defect which second position is a position in a longitudinal direction of the separator original sheet. The expression "longitudinal direction of the separator original sheet" refers to the direction in which a workpiece is conveyed during a process of producing a separator.

The above arrangement makes it possible to, on the basis of the information on the second position, easily find the defect when the separator original sheet is wound off.

The separator original sheet producing method in accordance with an embodiment of the present invention may preferably be arranged such that the defect information is recorded at a portion of the separator original sheet which portion corresponds to a second position of the defect which second position is a position in a longitudinal direction of the separator original sheet.

The above arrangement makes it possible to specify the second position of a defect on the basis of the position at which defect information has been recorded. Further, the defect information is recorded at a portion of the separator original sheet which portion corresponds to the second position of the defect. Thus, even in a case where the separator original sheet has been stretched lengthwise, the lengthwise position of the defect is substantially not displaced from the lengthwise position of the defect information. The lengthwise position of a defect is thus easily specifiable even in the case where the separator original sheet has been stretched lengthwise.

In order to attain the above object, a separator producing method in accordance with an embodiment of the present invention includes the steps of: (a) forming a separator original sheet; (b) detecting a defect in the separator original sheet; (c) recording defect information including information on a first position of the defect which first position is a position in a width direction of the separator original sheet; (d) cutting the separator original sheet having the defect, of which the information has been recorded in the step (c), in a longitudinal direction of the separator original sheet into a plurality of separators; (e) reading the information; and (f) on a basis of the information read in the step (e), providing at least one of the plurality of separators with a mark for specifying a position of the defect.

This feature involves providing, on the basis of the information read in the step (e), at least one of the plurality of separators with a mark for specifying the position of a defect. This makes it possible to easily remove a defective portion of a separator among the plurality of separators, prepared by slitting a separator original sheet, which separator has the defect.

The separator producing method in accordance with an embodiment of the present invention may preferably further include the steps of: (g) winding up the at least one of the plurality of separators, which at least one of the plurality of separators has been provided with the mark; (h) sensing the mark while carrying out an operation of winding off the at least one of the plurality of separators, which has been wound up in the step (g), and winding up the at least one of the plurality of separators again; and (i) in accordance with the sensing of the mark, stopping the operation and removing the defect.

The above arrangement, which involves removing a defect after the separator is wound up, eliminates the need to stop the winding and thus improves the working efficiency.

The separator producing method in accordance with an embodiment of the present invention may preferably be arranged such that in the step (i): the at least one of the plurality of separators is cut in the width direction at two positions opposite to each other in the longitudinal direction with the defect therebetween; the defect is removed; and cut parts of the separator are then connected.

The above arrangement makes it possible to remove a defect in a separator original sheet for separator production.

The separator producing method in accordance with an embodiment of the present invention may preferably be arranged such that in the step (c), the information is recorded at a widthwise end of the separator original sheet.

The above arrangement makes it possible to recognize a defective portion by simply reading information recorded at a widthwise end of a separator original sheet.

The separator producing method in accordance with an embodiment of the present invention may preferably be arranged such that in the step (c), the information is recorded in an information storing device.

The above arrangement makes it possible to recognize a defective portion by reading information recorded in an information storing device.

The separator producing method in accordance with an embodiment of the present invention may preferably be arranged such that the step (f) is carried out by attaching a label.

In order to attain the above object, a separator original sheet in accordance with an embodiment of the present invention includes: at a widthwise end thereof, information on a position of a defect in the separator original sheet which position is a position in a width direction.

In order to attain the above object, a separator original sheet producing apparatus in accordance with an embodiment of the present invention includes: a forming section configured to form a separator original sheet; a defect detecting section configured to detect a defect in the separator original sheet; and a defect information recording section configured to record defect information including information on a position of the defect which position is a position in a width direction of the separator original sheet.

The present invention is not limited to the embodiments, but can be altered by a skilled person in the art within the scope of the claims. An embodiment derived from a proper combination of technical means each disclosed in a different embodiment is also encompassed in the technical scope of the present invention.

REFERENCE SIGNS LIST

4 Heat-resistant layer
6 Slitting apparatus (slitting section)
7 Cutting device (cutting machine)
12 Separator (film)
12a Heat-resistant separator, separator (film)
12b Heat-resistant separator original sheet, separator original sheet (film original sheet)
12c Separator original sheet
54 Coating section (film original sheet producing apparatus)
55 Base material defect inspecting device (defect detecting section, film original sheet producing apparatus)
57 Coating defect inspecting device (defect detecting section, film original sheet producing apparatus)
58 Pinhole defect inspecting device (defect detecting section, film original sheet producing apparatus)
56, 56a Defect information recording device (defect information recording section, film original sheet producing apparatus)
73 Reading section
74 Mark providing device (defect marking providing section)
75 Determining device (determining section)
81 Core
82 Core
83 Mark sensing device
84 Defect removing device
85 Connecting device
86 Outermost portion
91 Information storing device D Defect
DC, DC2 Defect code
L Mark

The invention claimed is:

1. A film producing method, comprising the steps of:
   (a) obtaining information on a position of at least one defect in a film; and
   (b) providing a plurality of markings at respective positions in a vicinity of the at least one defect, the plurality of markings indicating the position of the at least one defect,
   in the step (a), the information on the position indicating presence or absence of defectiveness in each of a plurality of divisional regions of a unit region having a predetermined length in a longitudinal direction of the film, the plurality of divisional regions being arranged in a width direction of the film,
   in the step (b), the plurality of markings including a pair of markings provided in such a manner that one of the pair of markings lies on a first side, in the longitudinal direction of the film, of a divisional region out of the plurality of divisional regions which divisional region has the at least one defect and that the other of the pair of markings lies on a second side, in the longitudinal direction of the film, of the divisional region having the at least one defect.

2. The film producing method according to claim 1, wherein
   in a case where the at least one defect includes a plurality of defects apart from each other in the longitudinal direction of the film by a distance of less than a predetermined value,
   a first marking out of the pair of markings is provided on the first side of a first defect out of the plurality of defects which first defect is farthest on the first side, and
   a second marking out of the pair of markings is provided on the second side of a second defect out of the plurality of defects which second defect is farthest on the second side.

3. The film producing method according to claim 1, further comprising the step of:
   (c) obtaining original sheet defect position information indicative of a position of the at least one defect in a film original sheet; and
   (d) slitting the film original sheet along a slit line, extending in a longitudinal direction of the film original sheet, so as to produce a plurality of films.

4. The film producing method according to claim 3, wherein:
   in the step (a), the information on the position is obtained on a basis of the original sheet defect position information; and
   in the step (b), the plurality of markings are provided to the film on a basis of the information on the position.

5. The film producing method according to claim 3, wherein:
   in the step (b), the plurality of markings are provided to the film original sheet on a basis of the original sheet defect position information; and
   in the step (d), the film original sheet, to which the plurality of markings have been provided, is slit.

6. The film producing method according to claim 5, wherein
   in the step (b), the plurality of markings are so provided as not to overlap the slit line.

7. The film producing method according to claim 3, wherein
   in the step (b), at least one of the plurality of markings is provided in a vicinity of the at least one defect in a first one of two films adjacent to each other via the slit line, and at least one other of the plurality of markings is provided at a portion of a second one of the two films which portion corresponds to a position of the at least one of the plurality of markings.

8. The film producing method according to claim 7, wherein
   in the step (c), the original sheet defect position information indicates presence or absence of defectiveness in each of a plurality of divisional regions arranged on a surface of the film original sheet in a width direction of the film original sheet, and
   in a case where in the step (d), the slit line divides at least one of the plurality of divisional regions which at least one divisional region has the at least one defect,
   in the step (b), the plurality of markings are provided to each of two films each including a divisional part of the at least one divisional region which divisional part results from slitting the film original sheet along the slit line.

9. A film producing apparatus, comprising:
   a defect information obtaining section configured to obtain information on a position of a defect in a film; and
   a defect marking providing section configured to provide a plurality of markings at respective positions in a vicinity of the defect, the plurality of markings indicating the position of the defect,
   the defect information obtaining section being configured to obtain, as the information on the position, information indicating presence or absence of defectiveness in each of a plurality of divisional regions of a unit region having a predetermined length in a longitudinal direction of the film, the plurality of divisional regions being arranged in a width direction of the film,
   the defect marking providing section being configured to provide a pair of markings in such a manner that one of the pair of markings lies on a first side, in the longitudinal direction of the film, of a divisional region out of the plurality of divisional regions which divisional region has the at least one defect and that the other of the pair of markings lies on a second side, in the longitudinal direction of the film, of the divisional region having the at least one defect.

* * * * *